US012070458B2

(12) United States Patent
Tran

(10) Patent No.: US 12,070,458 B2
(45) Date of Patent: *Aug. 27, 2024

(54) THERAPEUTIC AGENT COMPOSITION AND METHOD OF USE, FOR TREATMENT OF MILD CONGNITIVE IMPAIRMENT, DEPRESSION, AND PSYCHOLOGICAL DISORDERS

(71) Applicant: Lloyd Hung Loi Tran, San Jose, CA (US)

(72) Inventor: Lloyd Hung Loi Tran, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/315,910

(22) Filed: May 11, 2023

(65) Prior Publication Data

US 2023/0381175 A1 Nov. 30, 2023

Related U.S. Application Data

(63) Continuation of application No. 17/359,515, filed on Jun. 26, 2021, now abandoned, which is a continuation of application No. 16/412,759, filed on May 15, 2019, now Pat. No. 11,090,303.

(60) Provisional application No. 62/674,855, filed on May 22, 2018, provisional application No. 62/671,466, filed on May 15, 2018, provisional application No. 62/671,485, filed on May 15, 2018.

(51) Int. Cl.
| | |
|---|---|
| *A61K 31/4985* | (2006.01) |
| *A61K 9/00* | (2006.01) |
| *A61K 38/12* | (2006.01) |
| *A61K 38/30* | (2006.01) |
| *A61K 45/06* | (2006.01) |
| *A61P 25/24* | (2006.01) |
| *A61P 25/28* | (2006.01) |

(52) U.S. Cl.
CPC ........ *A61K 31/4985* (2013.01); *A61K 9/0019* (2013.01); *A61K 9/0053* (2013.01); *A61K 38/12* (2013.01); *A61K 38/30* (2013.01); *A61K 45/06* (2013.01); *A61P 25/24* (2018.01); *A61P 25/28* (2018.01)

(58) Field of Classification Search
CPC .............. A61K 31/4985; A61K 9/0019; A61K 38/12; A61K 9/0053; A61K 38/30; A61K 45/06; A61P 25/28; A61P 25/24
See application file for complete search history.

(56) References Cited

U.S. PATENT DOCUMENTS

| | | |
|---|---|---|
| 5,439,930 A | 8/1995 | Seredenin et al. |
| 6,124,361 A | 9/2000 | Chenard |
| 6,187,906 B1 | 2/2001 | Gluckman et al. |
| 6,251,865 B1 | 6/2001 | Clark |
| 6,258,582 B1 | 7/2001 | Acton |
| 6,284,778 B1 | 9/2001 | Zelle |
| 6,291,213 B1 | 9/2001 | Rothstein |
| 6,303,576 B1 | 10/2001 | Blaschuk et al. |
| 6,689,904 B2 | 2/2004 | Greenfield et al. |
| 6,969,702 B2 | 11/2005 | Bertilsson et al. |
| 7,232,798 B2 * | 6/2007 | Tran ........................ A61P 25/16 514/8.4 |
| 10,124,035 B2 | 11/2018 | Tsai et al. |
| 11,090,303 B2 * | 8/2021 | Tran ................... A61K 31/4985 |
| 2003/0109531 A1 | 6/2003 | Tran |
| 2006/0258663 A1 | 11/2006 | Brimble et al. |
| 2007/0244039 A1 | 10/2007 | Tran |
| 2009/0232775 A1 | 9/2009 | Bertilsson et al. |
| 2010/0247483 A1 | 9/2010 | Tran |
| 2011/0201614 A1 | 8/2011 | Bickerdike |
| 2015/0306171 A1 | 10/2015 | Tran |
| 2016/0263235 A1 | 9/2016 | Castaigne et al. |
| 2020/0054629 A1 | 2/2020 | Tran |

FOREIGN PATENT DOCUMENTS

| | | |
|---|---|---|
| EP | 0366638 A2 | 2/1990 |
| EP | 0363944 B1 | 4/1990 |
| EP | 0363994 A2 | 4/1990 |

(Continued)

OTHER PUBLICATIONS

Abdipranoto, Andrea, Sara Wu, Sandy Stayte and Bryce Vissel—The Role of Neurogenesis in Neurodegenerative Diseases and its Implications for Therapeutic Development—CNS & Neurological Disorders—Drug Targets, 2008, 7, 187-210 187.
Belousov et al., Economic Aspects of Second Generation Insulin Analogs in Diabetes Mellitus Type 2, Kachestvennaya klinicheskaya praktika (2019) 1:4-11.
Berg, D. A., Su, Y., Jimenez-Cyrus, D., Patel, A., Huang, N., Morizet, D., et al. (2019). A common embryonic origin of stem cells drives developmental and adult neurogenesis. Cell 177:e615.
Boldrini, M., Fulmore, C. A., Tartt, A. N., Simeon, L. R., Pavlova, I., Poposka, V., . . . Mann, J. J. (2018). Human Hippocampal Neurogenesis Persists throughout Aging. Cell Stem Cell, 22(4), 589-599.e5. doi:10.1016/j.stem.2018.03.015.

(Continued)

*Primary Examiner* — Olga N Chernyshev
(74) *Attorney, Agent, or Firm* — David R. Preston

(57) ABSTRACT

The present invention generally relates to the use of cyclic Prolyl Glycine ("cyclic PG" or "cPG") and analogues and mimetics thereof, as neuroprotective agents for the treatment and or prevention of cognitive impairment and neurological disorders including but not limited to cerebral ischemia or cerebral infarction, status epilepticus, perinatal asphyxia, anoxia, and cerebral trauma, as well as to the treatment and prevention of chronic neurodegenerative disorders such as Alzheimer's disease, Parkinson's disease, and Dementia with Lewy Bodies. The present invention also generally provides manufacturing methods to prepare dosage forms. The present invention further generally relates to the use of cyclic Prolyl Glycine and analogues and mimetics thereof, as neuroprotective and neuro-regenerating agents for the treatment and or prevention of depression and other psychological disorders.

19 Claims, 15 Drawing Sheets

(56) References Cited

FOREIGN PATENT DOCUMENTS

| | | |
|---|---|---|
| EP | 0363994 A3 | 3/1991 |
| EP | 0363994 B1 | 9/1993 |
| NZ | 515371 | 11/2001 |
| NZ | 515432 | 11/2001 |
| WO | WO 93/02695 A1 | 2/1993 |
| WO | WO 95/17204 A1 | 6/1995 |
| WO | WO 98/36764 A2 | 8/1998 |
| WO | WO 99/47490 A1 | 9/1999 |
| WO | WO 01/34631 A2 | 5/2001 |
| WO | WO 03/039487 A2 | 5/2003 |
| WO | WO 03/039487 A3 | 5/2003 |
| WO | WO 03/041655 A2 | 5/2003 |
| WO | WO 19/222339 A1 | 11/2019 |

OTHER PUBLICATIONS

Boyko S., Kolyasnikova K., Zherdev V. Comparative pharmacokinetics and pharmacodinamics of noopept, its activity metabolite cycloprolylglycine and piracetam. Pharmacokinetics and Pharmacodynamics. 2019;(3):34-38. (In Russ.) https://doi.org/10.24411/2588-0519-2019-10053.

Chuang, T.T. (2010).Neurogenesis in mouse models of Alzheimer's disease. Biochim. Biophys. Acta 1802, 872-880. doi:10.1016/j.bbadis.2009.12.008.

DeCarolis, N. A., & Eisch, A. J. (2010). Hippocampal neurogenesis as a target for the treatment of mental illness: A critical evaluation. Neuropharmacology, 58(6), 884-893. doi:10.1016/j.neuropharm.2009.12.013.

Dietz V. et al., Neurological aspects of spinal-cord repair: promises and challenges. Lancet Neurol. 2006, 5:688-694.

Fuster-Matanzo, Almudena, María Llorens-Martín, Félix Hernández, and Jesús Avila—Role of Neuroinflammation in Adult Neurogenesis and Alzheimer Disease: Therapeutic Approaches—Mediators of Inflammation—vol. 2013 |Article ID 260925—https://doi.org/10.1155/2013/260925.

Gage, Fred H., Gerd Kempermann, Theo D. Palmer, Daniel A. Peterson, Jasodhara Ray—Multipotent progenitor cells in the adult dentate gyrus—Journal of Neurobiology vol. 36, Issue 2—Jan. 6, 1999—https://doi.org/10.1002/(SICI)1097-4695(199808)36:2<249::AID-NEU11>3.0.CO;2-9.

Gage, F., Neurogenesis in the Adult Brain, J. Neuroscience, 22(3):612-613 (2002).

Gangemi et al., Journal of Neurochemistry, 2004, 89:286-306.

Garibova et al., Doklay Biochemistry and Biophysics, 2019, 488:324-326.

Gouras, G., & Fillit, H. (2006). Neurogenesis as a Therapeutic Strategy for Cognitive Aging and Alzheimers Disease. Current Alzheimer Research, 3(1), 3-3. doi:10.2174/156720506775697151.

Gudasheva TA et al., Identification of a novel endogenous memory facilitating cyclic dipepetide cyclo-prolylglycine in rat brain, FEBS Lett. 1996, 391:149-152 (1996).

Gudasheva et al., European Journal of Drug Metabolism and Pharmacokinetics 1997, 22(3):245-252.

Gudasheva, T.A., Koliasnikova, K.N., Antipova, T.A., Academician Seredenin, S.B., 2016. Neuropeptide cycloprolylglycine increases the levels of brain-derived neurotrophic factor in neu-ronal cells. Biochemistry and Biophysics 469, 273-276.

Gudasheva, T. A., Grigoriev, V. V., Koliasnikova, K. N., Zamoyski, V. L., & Seredenin, S. B. (2016). Neuropeptide cycloprolylglycine is an endogenous positive modulator of AMPA receptors. Doklady Biochemistry and Biophysics, 471(1), 387-389. doi:10.1134/s160767291606003x.

Gulati, A., Understanding neurogenesis in the adult human brain, Indian J. Pharmacol, 47(6):583-584 (2015).

Henrich-Noack et al., TGF-BI Protects Hippocampal Neurons Against Degeneration Caused by Transient Global Ischemia, Stroke, 27:1609-1615, 1996.

Hollands C., Bartolotti N. and Lazarov O., (2016) Alzheimer's Disease and Hippocampal Adult Neurogenesis; Exploring Shared Mechanisms. Front.Neurosci.10:178. doi: 10.3389/fnins.2016.00178.

Jackowski A. et al., Neural injury repair: hope for the future as barriers to effective CNS regeneration become clearer. Brit. J. Neurosurg. 1995, 9:303-317.

Jin, K., Xie, L., Mao, X. O., & Greenberg, D. A. (2006). Alzheimer's disease drugs promote neurogenesis. Brain Research, 1085(1), 183-188. doi:10.1016/j.brainres.2006.02.081.

Jourdi, H., Hsu, Y.-T., Zhou, M., Qin, Q., Bi, X., and Baudry, M.—Positive AMPA. receptor modulation rapidly stimulates BDNF release and increases dendritic mRNA translation. J. Neurosci., 2009, vol. 29, No. 27, pp. 8688-8697.

Kemperman, G., Adult neurogenesis: an evolutionary perspective, Cold Spring Harb. Perspect. Biol. 8:a018986 (2016).

Kolyasnikova et al., Synthesis and Pharmacological Activity of Analogs of the Endogenous Neuropeptide Cycloprolylglycine, Pharmaeutical Chemistry Journal 46(2) 96-102 (2012).

Kolyasnikova, K.N., Nazarova, G.A., Gudasheva, T.A., Voron-ina, T.A., Seredenin, S.B., 2015. Antihypoxic Activity of Cycloprolylglycine Analogs. Bulletin of Experimental Biology and Medicine 158 (4), 458-460.

Kolyasnikova, K.N., Kuznetsova, E.A., Nikolaev, S.V. et al. Structure-Activity (Antihypoxic) Relationship in a Series of Substituted Glyprolines. Pharm Chem J 52, 501-505 (2018). https://doi.org/10.1007/s11094-018-1848-8.

Lee, H., & Thuret, S. (2018). Adult Human Hippocampal Neurogenesis: Controversy and Evidence. Trends in Molecular Medicine, 24(6), 521-522, doi:10.1016/j.molmed.2018.04.002.

Liu et al, Experimental Neurology, 2004, 189:199-203.

Ming G., et al., Adult neurogenesis in the mammalian brain: significant answers and significant questions, Neuron 70(4):687-702 (2011).

Mira H and Morante J (2020)—Neurogenesis From Embryo to Adult—Lessons From Flies and Mice. Front. Cell Dev. Biol. 8:533. doi: 10.3389/fcell.2020.00533.

Mohapel, P., Leanza, G., Kokaia, M., & Lindvall, O. (2005). Forebrain acetylcholine regulates adult hippocampal neurogenesis and learning. Neurobiology of Aging, 26(6), 939-946. doi: 10.1016/j.neurobiolaging.2004.07.015.

Moreno-Jiménez, E.P., Flor-García, M., Terreros-Roncal, J. et al. Adult hippocampal neurogenesis is abundant in neurologically healthy subjects and drops sharply in patients with Alzheimer's disease. Nat Med 25, 554-560 (2019). https://doi.org/10.1038/s41591-019-0375-9.

Mu, Yangling and Fred H Gage—Adult hippocampal neurogenesis and its role in Alzheimer's disease—Molecular Neurodegeneration 2011, 6:85.

Paredes, M. F., Sorrells, S. F., Cebrian-Silla, A., Sandoval, K., Qi, D., Kelley, K. W., . . . Alvarez-Buylla, A. (2018). Does Adult Neurogenesis Persist in the Human Hippocampus? Cell Stem Cell, 23(6), 780-781. doi:10.1016/j.stem.2018.11.006.

Povarnina, P.Yu., Kolyasnikova, K.N., Nikolaev, S.V., Antipova, T.A., Gudasheva, T.A., 2016. Neuropeptide cycloprolyl-glycine exhibits neuroprotective activity after systemic admin-istration to rats with modeled incomplete global ischemia and in in vitro modeled glutamate neurotoxicity. Bulletin of Experimental Biology and Medicine 160 (5), 653-655.

Prud'homme GJ et al., The inhibitory effects of transforming growth factore-beta-1. (TGF-beta 1) in autoimmune disease. J. Autoimmunity, 2000, 14:23-42 (2000).

Rishton, G. (2008). Small Molecules that Promote Neurogenesis in vitro. Recent Patents on CNS Drug Discovery, 3(3), 200-208. doi:10.2174/157488908786242425.

Tarrt et al, Consideratons for Assessing the Extent of Hippocampal Neurogenesis in the Adult and Aging Human Brain, Cell Stem Cell, 23 (Dec. 6, 2018).

Tatebayashi, Y., Lee, M.H., Li, L. et al. The dentate gyrus neurogenesis: a therapeutic target for Alzheimer's disease. Acta Neuropathol 105, 225-232 (2003). https://doi.org/10.1007/s00401-002-0636-3.

Taupin, Philippe, Neurogenesis and Alzheimer's Disease—Drug Target Insights 2006: 1 1-4.

(56) References Cited

OTHER PUBLICATIONS

Taupin, P. (2010). A Dual Activity of ROS and Oxidative Stress on Adult Neurogenesis and Alzheimers Disease. Central Nervous System Agents in Medicinal Chemistry, 10(1), 16-21. doi:10.2174/187152410790780172.

Taupin, P. (2010). Adult neurogenesis and neural stem cells as a model for the discovery and development of novel drugs. Expert Opinion on Drug Discovery, 5(10), 921-925. doi: 10.1517/17460441.2010.512038.

Vasileva, E., Abdullina, A., Kondrakhin, E., & Kovalev, G. (2019). Antidepressant-like activity of cyclo-l-prolylglycine. European Neuropsychopharmacology, 29, S544-S545. doi: 10.1016/j.euroneuro.2018.11.804.

Winner, B, et al., Adult neurogenesis in neurodegenerative disease, Cold Spring Harb. Perspect. Biol. 7:a02187 (2015).

\* cited by examiner

Figure 2

Time for rats to reach the platform

Figure 7: Graph showing the impact of BrdU + Cells/300 micrometer at sub ventricular zone for cPG, cGMeP and c(PG)3 drug solutions
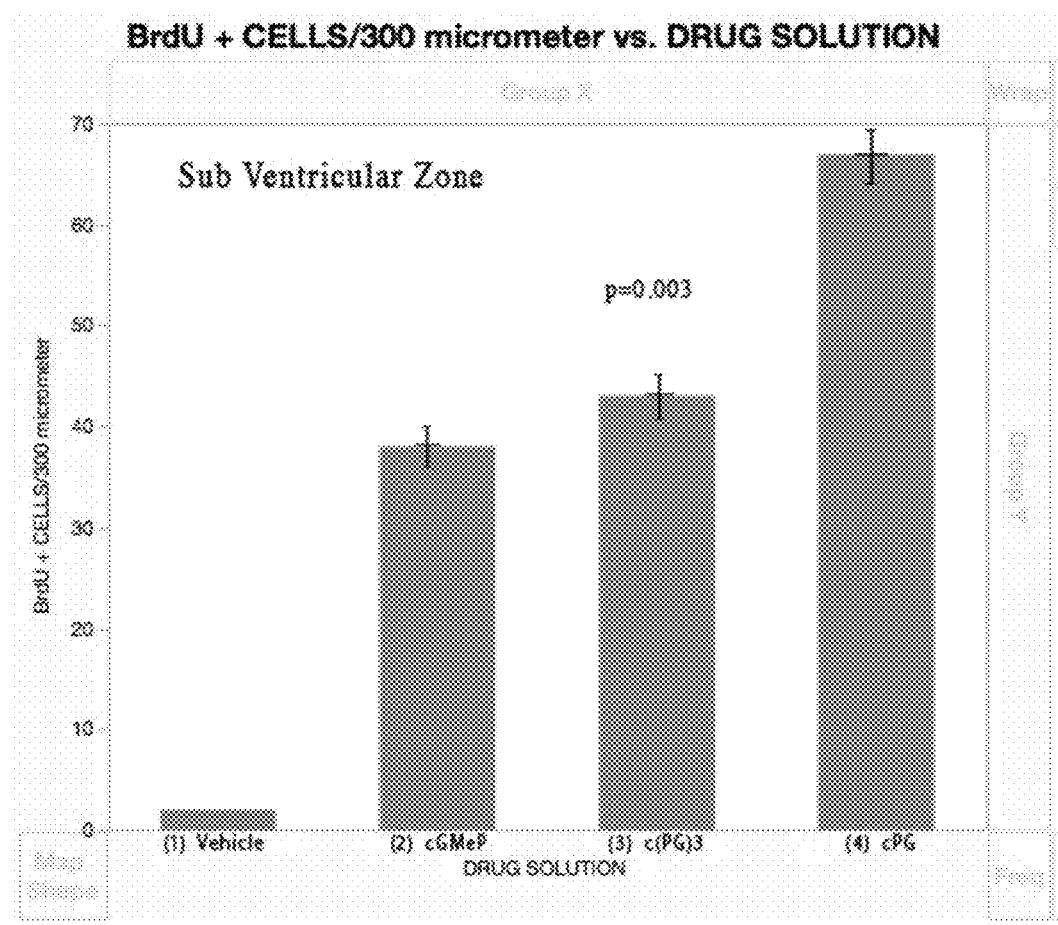

Figure 8. Graph showing the impact of BrdU + Cells/300 micrometer at dentate gyrus for cPG, cGMeP and c(PG)3 drug solutions
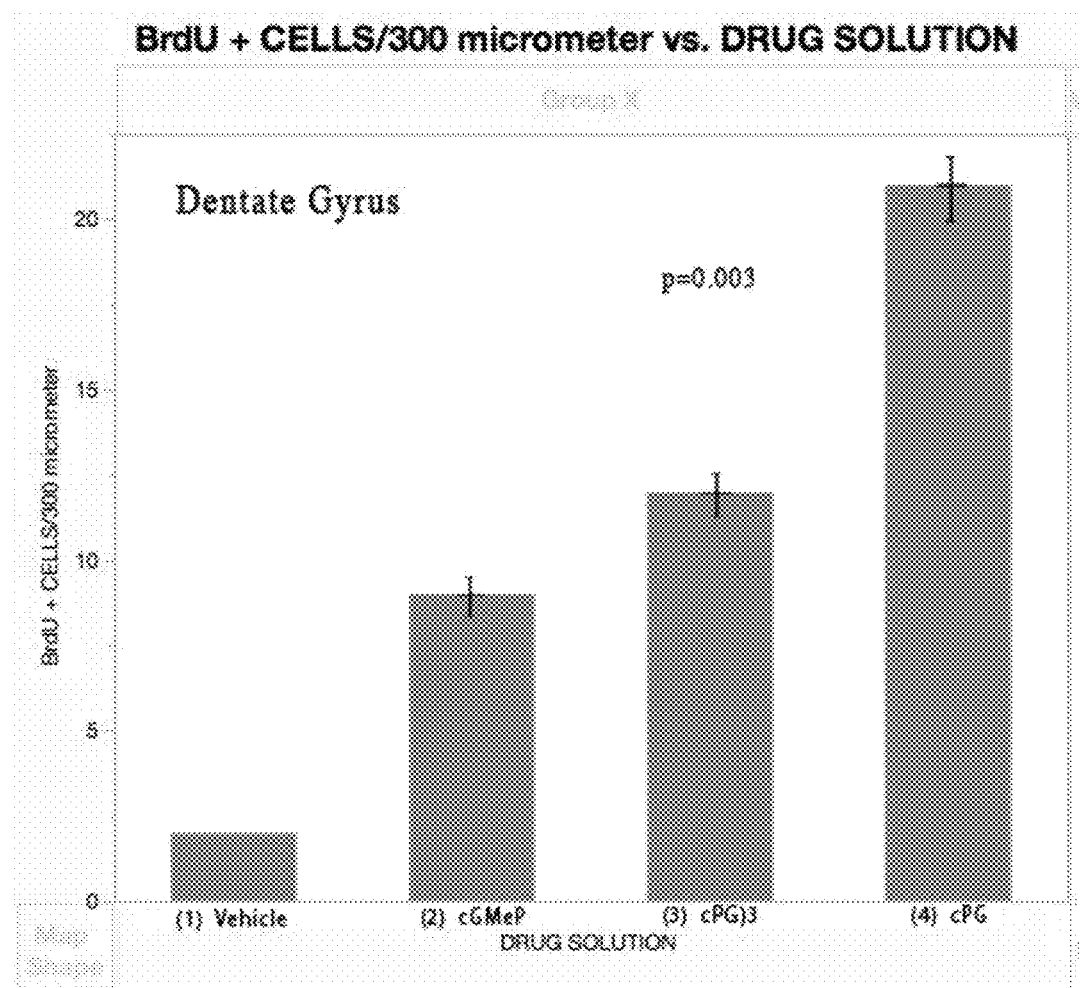

Figure 9: illustrate the improvement in the Ability to Concentrate and Count
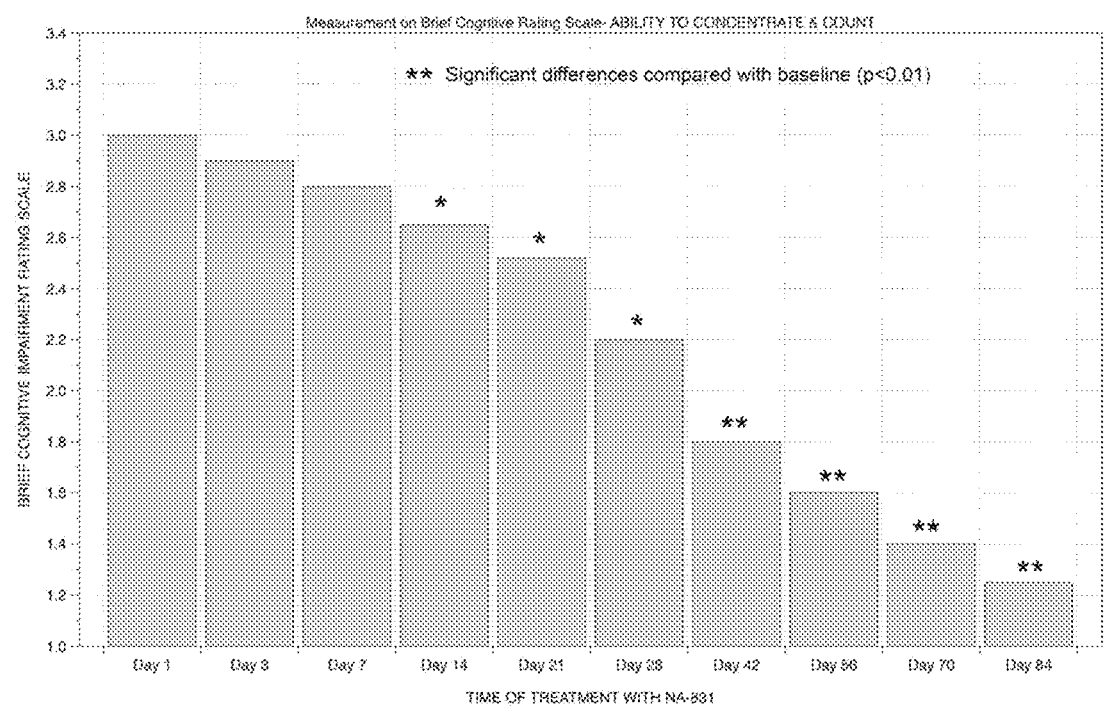

Figure 10: illustrates the improvement in Short Term Memory
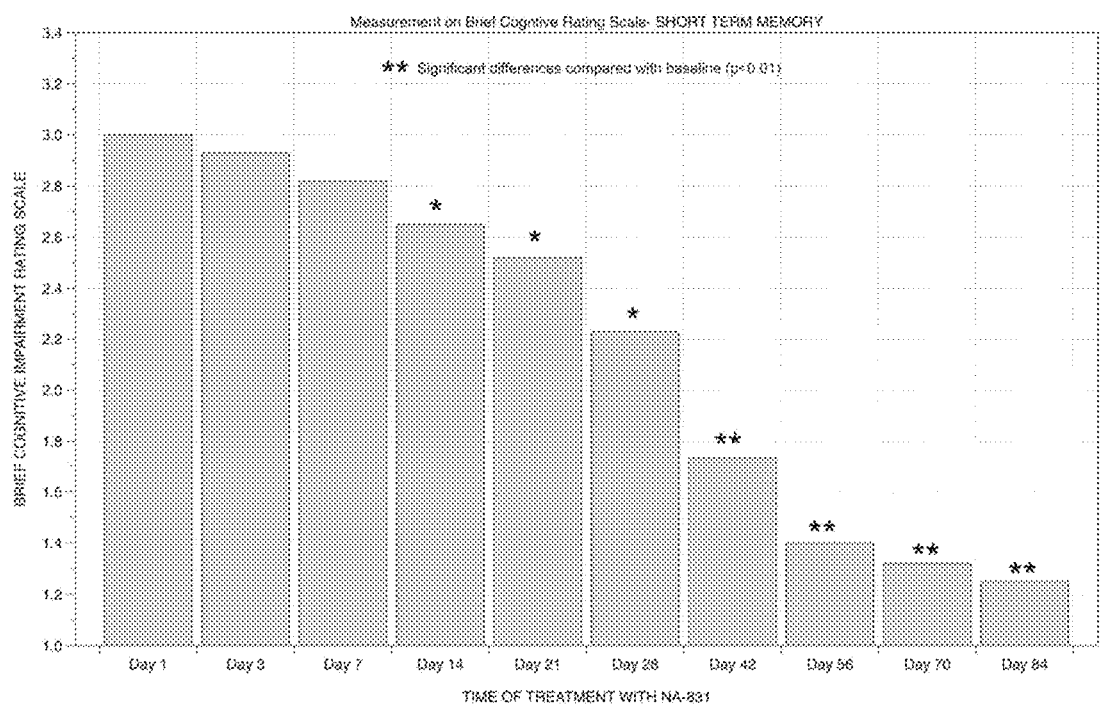

Figure 11: illustrates the improvement in Long Term Memory
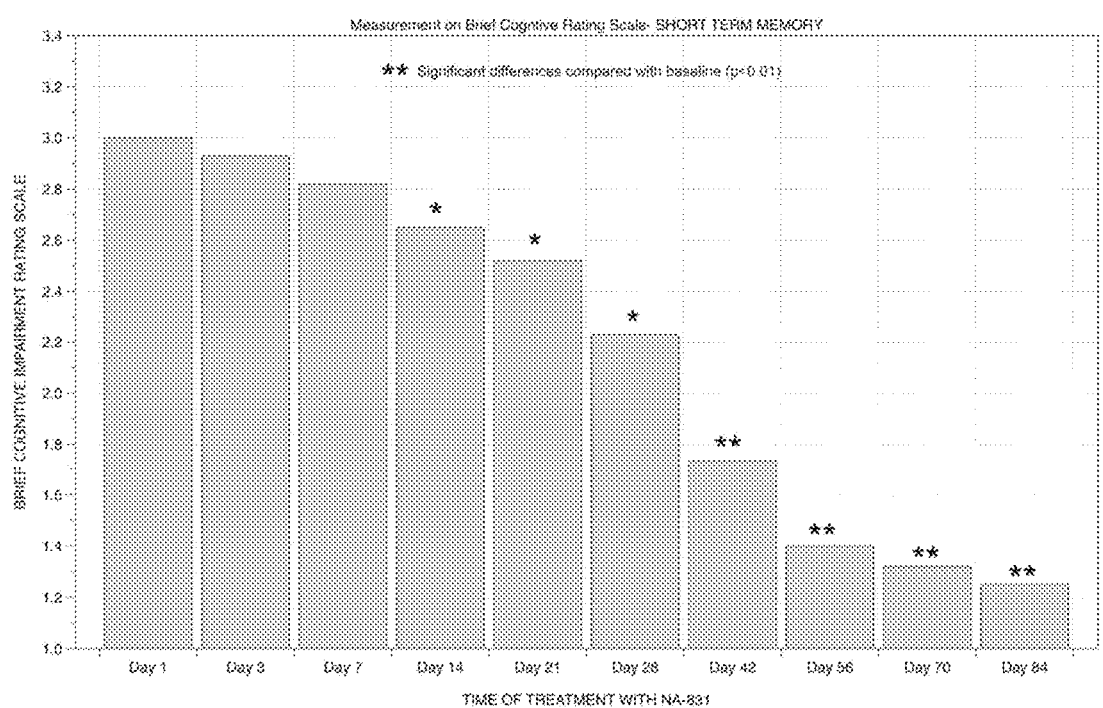

Figure 12: illustrates the Impact on Orientation
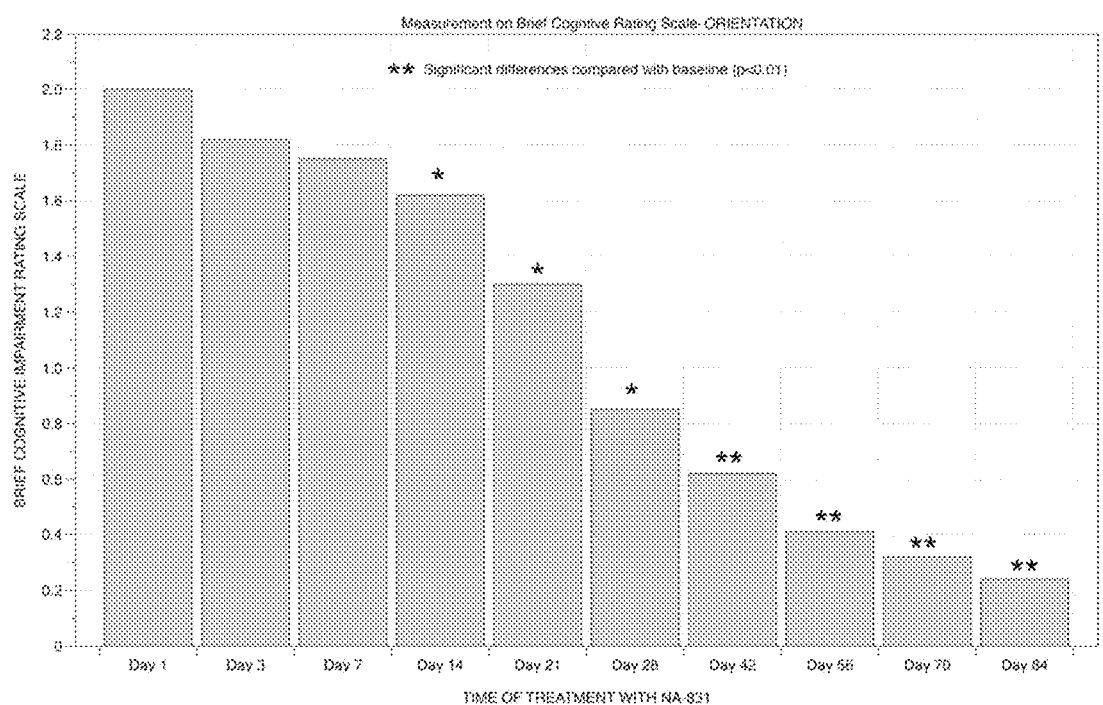

Figure 13: illustrates the improvement in Daily Activities and Self-Care
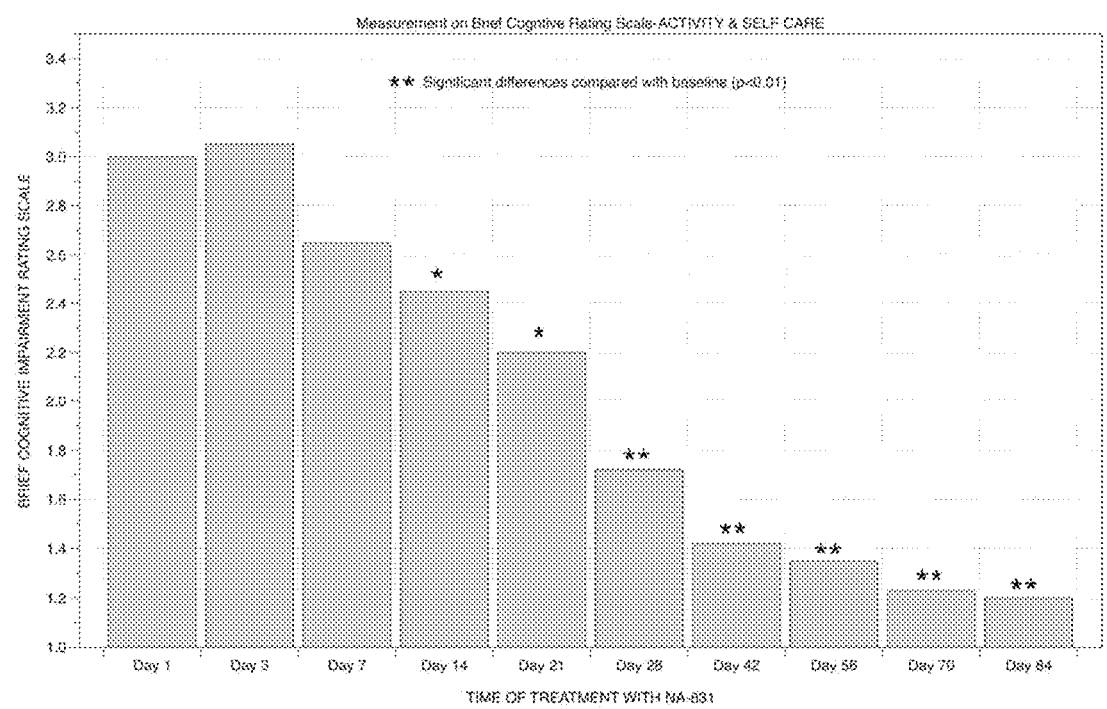

Figure 14: illustrates the Impact on Emotion
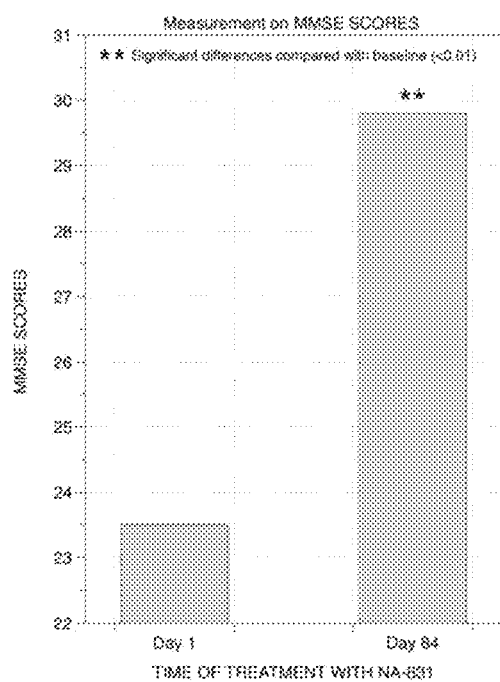

Figure 15: illustrates the Impact of Cognitive Capacity
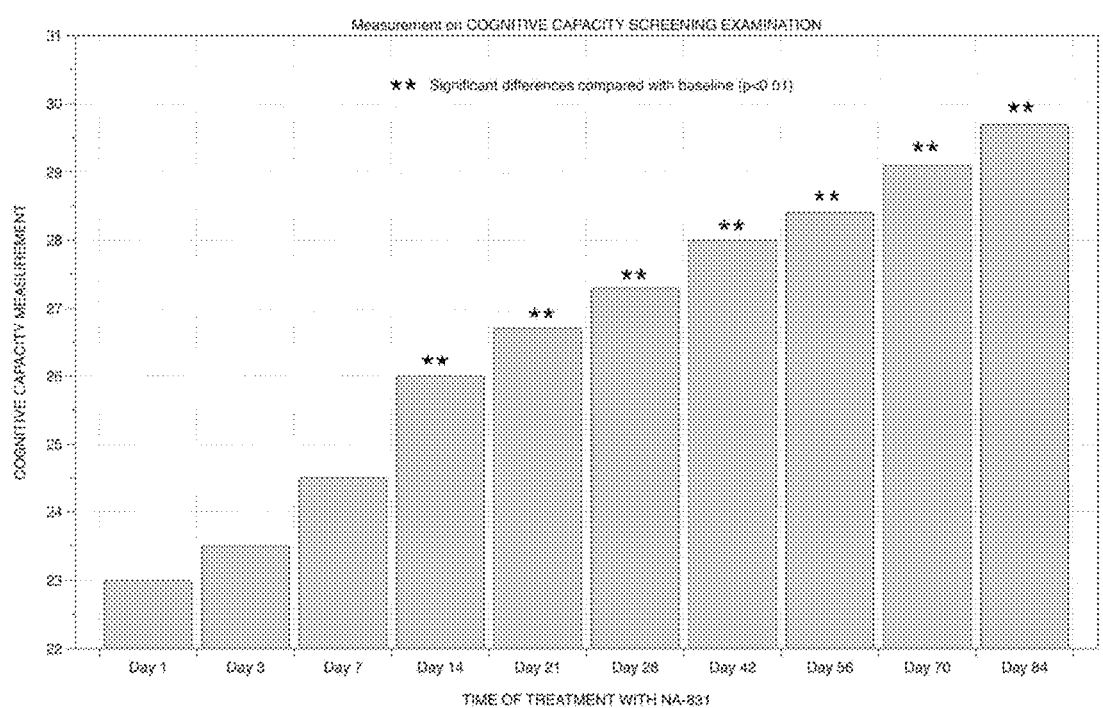

THERAPEUTIC AGENT COMPOSITION AND METHOD OF USE, FOR TREATMENT OF MILD CONGNITIVE IMPAIRMENT, DEPRESSION, AND PSYCHOLOGICAL DISORDERS

CROSS-REFERENCE TO RELATED APPLICATIONS

The present application is:
a Continuation of U.S. patent application Ser. No. 17/359,515, filed Jun. 26, 2021, which is
a Continuation of U.S. patent application Ser. No. 16/412,759, filed May 15, 2019, now U.S. Pat. No. 11,090,303, issued Aug. 17, 2021; which claims benefit of priority to:
U.S. Provisional Patent Application Ser. No. 62/674,855, filed May 22, 2018,
U.S. Provisional Patent Application Ser. No. 62/671,485, filed May 15, 2018, and
U.S. Provisional Patent Application Ser. No. 62/671,466, filed May 15, 2018,
each of which is incorporated by reference herein in their entirety.

Inventor Lloyd Hung Loi Tran reflects a legal name change from Loi H. Tran.

FIELD OF THE INVENTION

The present invention generally relates to novel cyclic dipeptides compounds structurally related to diketopiperazines and methods for their therapeutic use. In particular, this invention relates to the neuroprotection and neurogenesis activity of such compounds. Particularly, the present invention relates to the use of cyclic prolyl glycine ("cyclic GP" or "cPG") and cPG analogues and cPG compounds, pharmacologically effective analogues thereof, and pharmaceutical compositions thereof in the treatment and prevention of cognitive impairment and related neurodegenerative disorders and psychological disorders. The present invention also generally relates to materials and methods of regenerating neurons and glial cells or a method of repairing damaged neurons and glial cells.

BACKGROUND

Mild cognitive impairment ("MCI") is a syndrome defined as cognitive decline greater than expected for an individual's age and education level. Mild cognitive impairments are those involving impairments of memory and other cognition functions, beyond the age norm but not leading to the characteristic of dementia.

The prevalence of MCI varies by age. The prevalence of MCI among different age groups is as follows: 6.7% for ages 60-64; 8.4% for ages 65-69, 10.1% for ages 70-74, 14.8% for ages 75-79, and 25.2% for ages 80-84. More than half progress of people with MCI progress to dementia within 5 years. (Petersen R C, Lopez O, Armstrong M J, Getchius T, Ganguli M, Gloss D, Gronseth G S, Marson D, Pringsheim T, Day G S, Sager M, Stevens J, Rae-Grant A (January 2018). "Practice guideline update summary: Mild cognitive impairment— Report of the Guideline Development, Dissemination, and Implementation Subcommittee of the American Academy of Neurology". *Neurology*. Special article. 90 (3): 1-10.:10.1212/WNL.0000000000004826. https://en.wikipedia.org/wiki/PubMed_Identifier"\o"PubMed Identifier 29282327.)

Dementia is an overall term that describes a group of symptoms associated with a decline in memory or other thinking skills severe enough to reduce a person's ability to perform everyday activities. Alzheimer's disease accounts for 60 to 80 percent of these types of cases. Vascular dementia, which occurs after a stroke, is the second most common dementia type. But there are many other conditions that can cause symptoms of dementia, including some that are reversible, such as thyroid problems and vitamin deficiencies. While symptoms of dementia can vary greatly, at least two of the following core mental functions are to be significantly impaired to be considered dementia: memory, communication and language, ability to focus and pay attention, reasoning and judgment, and visual perception.

There are more than 5.5 million people in the US and 50 million people worldwide that have Alzheimer's disease in 2018. (Ref: Alzheimer's Disease International's World Alzheimer Report 2018) The growth in the prevalence of Alzheimer's disease over the next few decades is anticipated to result in great pressure on the social and health-care systems of developed and developing economies alike. There is a long unmet need for therapies that halt, substantially slow, slow or otherwise ameliorate the progression, symptoms, or provide comfort or palliative care of this disease and related diseases.

Ramon y Cajal, a pioneer researcher in the early 20th century wrote: "The functional specialization of the brain imposed on the neurons two great lacunae; proliferative inability and irreversibility of intraprotoplasmatic differentiation. It is for this reason that, once the development was ended, the founts of growth and regeneration of the axons and dendrites dried up irrevocably."(Ramón y Cajal, Santiago; L. Azoulay (1894). Les nouvelles idées sur la structure du système nerveux chez l'homme et chez les vertébrés' (New ideas on the fine anatomy of the nerve centres). This hypothesis, while previously being considered the fundamental principle of neuroscience dated back in the late $19^{th}$ century to the mid-$20^{th}$ century, has now been proved invalid.

In 1966 Altman and Gopal demonstrated the evidence of adult mammalian neurogenesis was found in rodent hippocampus and other region of the brain. He reported the autoradiographic and histological studies of postnatal neurogenesis, in which cell proliferation and migration in the anterior forebrain, with special reference to persisting neurogenesis in the olfactory bulb. ((Altman J. (1966) and D. Gopal. "Autoradiographic and histological evidence of postnatal hippocampal neurogenesis in rats" Journal of Comparative Neurology—Volume 124, Issue 3, June 1965 (https://doi.org/10.10021/cne.901240303)).

In Altman's experiment, the intact adult mammalian brain, neuroregeneration maintains the function and structure of the central nervous system (CNS). Thymidine-H3 was injected intraperitoneally into 6- and 13-day old rats and they lived afterwards for periods ranging from one hour to 60 days. Autoradiographic data obtained from animals surviving for short periods were used to estimate rates of regional cell proliferation. Animals with longer survival were used to deduce the movements of new cells from germinal sites, through migratory channels, to target areas, and to determine their mode of differentiation. The formation and differentiation of microneurons goes on during infancy, though in most structures at a declining rate. Cell multiplication continued at a very high rate in the external granular layer of the cerebellar cortex, whence cells migrated to the molecular layer and internal granular layer.

It has been shown that indeed adult regenerated neurons are integrated into the existing brain circuitry, and contribute to ameliorating neurological deficits (Nakatomi H. Kuriu T. Okabe S. Yamamoto S. Hatano O. Kawahara N. Tamura A. Kirino T. Nakafuku M—Regeneration of hippocampal pyramidal neurons after ischemic brain injury by recruitment of endogenous neural progenitors. Cell 110:429-441, 2002.

Interestingly, observations have also shown that neurogenesis is occurring not only at the level of the olfactory bulb and hippocampus. In this respect it has been suggested by Zhao et al. that this process can also occur in the adult mouse substantia nigra, opening up a new field of investigation for the treatment of neurogenerative diseases (Zhao Ni. Momma S. Delfani K. Carlen M. Cassidy R M. Johansson C B. Brismar H. Shupiiakov O. Frisen J. Janson A M (2003) Evidence for neurogenesis in the adult mammalian substantia nigra. Proc Natl Acad Sci USA 100:7925-79:30)

According to a review paper by Guo-li Ming, since the discovery of neurogenesis the postnatal rat hippocampus, investigators have now firmly established that active neurogenesis from neural progenitors continues throughout life in discrete regions of the central nervous systems (CNS) of all mammals, including humans. (Guo-li Ming H. S. (2005). "Adult Neurogenesis in the Mammalian Central Nervous System". Annu. Rev. Neurosci, 28: 223-250. PMID 16022595)

Significant progress has been made in understanding the developmental process and regulation of adult neurogenesis, including proliferation, fate specification, neuronal maturation, targeting, and synaptic integration of the newborn neurons.

While the exact mechanism that maintains functional neural stem cells (NSCs) in these regions is elusive, NSCs have shown an ability to restore neurons and glia in response to certain pathological conditions.

Depression is a mental health disorder characterized by persistently depressed mood or loss of interest in activities, causing significant impairment in daily life. It is a very common condition that affects about 1 in every 5 individuals in the U.S. Many factors can cause depression, including genes, factors such as stress and brain chemistry. According to John Geddes, professor of epidemiological psychiatry at Oxford University. "depression is the single largest contributor to global disability that we have—a massive challenge for humankind," It affects around 350 million people worldwide and instances has risen almost 20% from 2005-2015 (World Health Organization and Center for Disease Control).

In recent years, much research effort has been invested in the study of mental depression and to methods for its treatment. While a number of drugs in the market can ameliorate depression, they all have undesirable side effects. It has recently been reported that one of the serious side effects of depression is suicide which has virtually become a sole cause of death from mental illness.

The present invention provides a method for the treatment of depression without serious side effects. According to this method, cyclic Prolyl Glycine and its pharmacologically effective analogues have been demonstrated as a potential treatment a patient suffering from depression.

SUMMARY OF THE INVENTION

One aspect the invention provides cyclic Prolyl Glycine compounds suitable for the treatment and prevention of disease and injury in animals and humans. The cyclic PG being selected from the group that includes cPG, cPG analogues, cPG peptidomimetics and relating compounds which promote or cause the formation of cPG or cPG analogues in vivo.

One example of cPG analogues is cyclic (glycyl-L-prolylglycyl-L-prolylglycyl-L-prolyl) or being abbreviated as cyclic(tri(Pro-Gly)) or referred herein as c(PG)3.

Another example of the cPG analogues is cyclic Glycyl-2-Allyl Proline, or cyclic Glycyl-Alkyl Proline referred herein as "cGAL."

Collectively the cPG, c(PG)3, cGAL, and Cyclic Glycyl-2-Methyl-Proline, and their pharmaceutically acceptable salts, are referred herein collectively as the "cPG compounds."

Also, Cyclic Glycyl-2-Methyl-Proline is a compound belong to the cyclic Glycyl-2-Alkyl Proline) group of compounds.

Furthermore, any of the cPG compounds, derivatives thereof, analogs thereof, and the like as disclosed herein or otherwise known in the art can be provided in the form of a pharmaceutically acceptable salt.

Preferably the cPG compounds are administered in a pharmaceutically acceptable composition such as a pharmaceutically acceptable carrier.

More preferably the composition additionally includes a therapeutic amount of a cPG compound in combination with a compound selected from growth factors and associated derivatives (insulin-like growth factor-I (IGF-I), insulin-like growth factor-II (IGF-II), GPE, transforming growth factor-ill, activin, growth hormone, nerve growth factor, growth hormone binding protein, JQF-binding proteins (especially JGFBP-3), basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1) FHF-2 FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\beta,\alpha,\chi$ or consensus interferon, TNF-$\alpha$; clomethiazole; kynurenic acid, Semax, FK506 [tacrolimus], L-threo-1-pheyl-2-decanoylamino-3-morpholino-1-propanol, andrenocorticotropin-(4-9_analogue [ORG2766] and dizolcipine [MK-801], selegiline; glutamate ants such as, NPS1506, GV1505260, MK-801, GV150526; AMPA ants such as 2,3-dihydroxy-6-nitro-7-sulfamoylbenzo (f)quinoxaline (NBQX), LY303070 and LY300164; anti-inflammatory agents directed against the addressin MAdCAM-1 and/or it integrin $\alpha$4 receptors ($\alpha$4$\beta$1 and $\alpha$4$\beta$7), such as anti-MAdCAM-11mAb MECA-367 (ATCC accession no. (HB-9478), interferons including interferon beta lb and interferon alfacon-1.

Preferably the cPG compounds can be used in the treatment or prevention of cell damage or cell death in response to diseases and injury resulting from septic shock, ischemia, administration of cytokines, overexpression of cytokines, ulcers, gastritis, ulcerative colitis, Crohn's disease, diabetes, rheumatoid arthritis, asthma, Alzheimer's disease, Parkinson's disease, multiple sclerosis, stroke, cirrhosis, allograft rejection, transplant rejection, encephalomyelitis, meningitis, pancreatitis, peritonitis, vasculitis, lymphocytic choriomeningitis glomerulonephritis, uveitis, glaucoma, blepharitis, chalazion, allergic eye disease, corneal ulcer, keratitis, cataract, retinal disorders, age-related macular degeneration, optic neuritis ileitis, inflammation induced by overproduction of inflammatory cytokines, hemorrhagic shock, anaphylactic shock, burn, infection leading to the overproduction of inflammatory cytokines induced by bacteria, virus, fungus, and parasites, hemodialysis, chronic fatigue syndrome, stroke, cancers, cardiovascular diseases associated with overproduction of inflammatory cytokines, heart disease, cardiopulmonary bypass, ischemic/reperfusion injury, ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, neuroblastoma, malaria, hematologic cancers, myelofibrosis, lung injury, graft-versus-host disease, head injury, CNS trauma, hepatitis, renal failure, chronic hepatitis C, paraquat poisoning, transplant rejection and preservation, fertility enhancement, bacterial translocation, circulatory shock, traumatic shock, hemodialysis, hangover, and combinations of two or more thereof.

Preferably the cPG compounds can be used in the restoration of myelination of axons in mammals where myelin depleted due to neural injury or disease.

Preferably cPG compound can be used in the restoration of myelination where depletion due to trauma, toxin exposure, asphyxia or hypoxia-ischemia, perinatal hypoxic-ischemic injury, injury to or disease of the white matter of the CNS, acute brain injury, chronic neurodegenerative disease including multiple sclerosis, and demyelinating diseases and disorders including acute disseminated encephalomyelitis, optic neuritis, transverse myelitis, Devic's disease, the leucodystrophies; non-inflammatory involvement; progressive multifocal leukoencephalopathy, and central pontine myelinolysis.

Preferably the cPG compound can be administered in combination with IGF-1 or an interferon.

Another related aspect the invention relates to a method of treating or preventing cell damage or cell death in response to injury and disease by administering at least one cPG compound.

Preferably, the cPG compound can be administered at between about 1 μg to about 150 mg per kilogram of bodyweight. A suitable dosage for administration of cPG can be, for example, preferably but not limited to between about 0.1 mg to about 100 mg per kilogram of body weight, between about 1 mg to about 100 mg per kilogram of body weight, between about 5 mg and about 70 mg per kilogram of body weight, between about 10 mg to about 50 mg per kilogram of body weight, or between about 20 mg to about 40 mg per kilogram of bodyweight. The dose, route of administration, and regime of cPG may be different for different diseases, disorders, and conditions. As an example, mild cognitive impairment may have a lower dose using the same or different route of administration than for Alzheimer's disease.

For example: a typical dosage for patient with mild cognitive impairment can be between about 0.2 mg to about 1 mg per day administered orally (for example, taking 1 capsule of 20 mg or 2 capsules per day per doctor prescription). Whereas, a more severe Alzheimer's Disease or severe Traumatic Brain injury patent can be administered intravenously in a range from between about 50 mg to about 300 mg per day. The particulars of the dose, route of administration, and regime for a particular disease, disorder, or condition can be evaluated in general or for a particular subject or patient.

A further aspect the invention relates to a method of restoring the myelination of axons in a mammal in need of restored myelination due to neural injury or disease, comprising administering a therapeutic amount of a cPG compound, where a cPG compound comprises cPG, a biologically active cPG analogue such as c(PG)3 and cGAL, a biologically active cPG peptidomimetic, a compound that increases the concentration of cPG, or a compound that increases the concentration of cPG analogues, effective to restore myelination of axons in a mammal. In one aspect of the invention, the method of restoring myelination of axons comprising administering a therapeutic amount of a cPG compound comprises stimulation of astrocytes to promote remyelination. In another aspect of the invention, the method of restoring myelination of axons comprising administering a therapeutic amount of a cPG compound comprises stimulation of oligodendrocytes to produce myelin.

In yet another aspect of the invention, the method of restoring myelination of axons to a mammal in need of restored myelination further comprises administering a therapeutic amount of a cPG compound in combination with a compound selected from IGF-I or an interferon. In one aspect of the invention, the method of restoring myelination of axons comprising administering a therapeutic amount of a cPG compound in combination with IGF-I or an interferon to stimulate astrocytes to promote remyelination. In another aspect of the invention, the method of restoring myelination of axons comprising administering a therapeutic amount of cPG in combination with IGF-I or an interferon to stimulate oligodendrocytes to produce myelin. In preferred embodiments, the interferon comprises interferon beta 1b (Betaseron). In a further most preferred embodiment, the interferon comprises consensus interferon (Infergen®, interferon alfacon-1).

In still a further aspect of the invention, the methods to treat or prevent cell damage and death in response to injury and disease, comprises administration of a therapeutic amount of a cPG compound, preferably but not limited to an amount from between about 10 μg to about 150 mg of cPG per kg of body weight of the mammal. A suitable dosage for administration of cPG can be, for example, preferably but not limited to between about 0.1 mg to about 100 mg per kilogram of body weight, between about 1 mg to about 100 mg per kilogram of body weight, between about 5 mg and about 70 mg per kilogram of body weight, between about 10 mg to about 50 mg per kilogram of body weight, or between about 20 mg to about 40 mg per kilogram of bodyweight. The dose, route of administration, and regime of cPG may be different for different diseases, disorders, and conditions. As an example, mild cognitive impairment may have a lower dose using the same or different route of administration than for Alzheimer's disease. For example: a typical dosage for patient with mild cognitive impairment may be between about 10 mg to about 50 mg per day administered orally (taking 1 capsule of 20 mg or 2 capsules per day per doctor prescription). Whereas, a more severe Alzheimer's Disease or severe Traumatic Brain injury patent may be administered intravenously in a range from between about 50 mg to about 300 mg per day. The particulars of the dose, route of administration, and regime for a particular disease, disorder, or condition can be evaluated in general or for a particular subject or patient.

In yet another aspect of the invention, the method of restoring myelination of axons to a mammal in need of restored myelination further comprises administering a therapeutic amount of a cPG compound in combination with IGF-1 from about 1 mg to about 10 mg of IGF-I per 1 Kg body weight of the mammal or an interferon from about 1.0 μg to about 10 μg of IGF-I per Kg of body weight of the mammal. In a preferred embodiment, the interferon is interferon beta. A suitable dosage for administration of cPG can be, for example, preferably but not limited to between about 0.1 mg to about 100 mg per kilogram of body weight, between about 1 mg to about 100 mg per kilogram of body weight, between about 5 mg and about 70 mg per kilogram of body weight, between about 10 mg to about 50 mg per kilogram of body weight, or between about 20 mg to about 40 mg per kilogram of bodyweight. The dose, route of administration, and regime of cPG may be different for different diseases, disorders, and conditions. As an example, mild cognitive impairment can have a lower dose using the same or different route of administration than for Alzheimer's disease. For example: a typical dosage for patient with mild cognitive impairment can be between about 10 mg to about 40 mg per day administered orally (taking 1 capsule of 20 mg or 2 capsules per day per doctor prescription). Whereas, a more severe Alzheimer's Disease or severe Traumatic Brain injury patent can be administered intravenously in a range from between about 50 mg to about 300 mg per day. The particulars of the dose, route of administration, and regime for a particular disease, disorder, or condition can be evaluated in general or for a particular subject or patient.

In a further preferred embodiment of the methods to treat or prevent cell damage and death in response to injury and disease, comprising administration of a cPG compound, the cPG compound is administered to the mammal through a shunt into a ventricle of the mammal.

In a further preferred embodiment of the methods to treat or prevent cell damage and death in response to injury and disease, comprising administration of a cPG compound, the cPG compound is administered to the mammal by peripheral administration.

The present invention provides a method of treatment for stimulating mature astrocytes to promote myelin production after hypoxic-ischemic injury including the step of increasing the active concentration of cPG and/or the concentration of analogues of cPG in the CNS of mammals.

Most preferably, it is the effective amount of IGF-I itself that is increased within the CNS of the mammal. This can be effected by direct administration of a cPG compound such as cPG, c(PG)3 or cGAL or cGMeP and indeed this is preferred. However, the administration of compounds that indirectly increase the effective amount of IGF-I (for example a pro-drug which, within the patient is cleaved to release cPG) is in no way excluded.

The active compound (IGF-I or its analogue or its mimetic) can be administered alone, or as is preferred, a part of a pharmaceutical composition.

The composition can be administered directly to the CNS. The latter route of administration can involve, for example, lateral cerebroventricular injection, focal injection or a surgically inserted shunt into the lateral cerebroventricle of the brain of the patient.

Conveniently, the stimulation and promotion of myelin production in oligodendrocytes and the support, stimulation and promotion of remyelination by mature astrocytes is promoted through the administration of cPG compounds in the prophylaxis or therapy of demyelinating diseases such as multiple sclerosis.

As generally described in U.S. Published patent application US20100247483A1 expressly incorporated herein fully by reference, cyclic Prolyl Glycine ("cyclic PG" or "cPG") has the following structure:

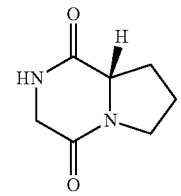

Structure 1 cyclic Prolyl Glycine (This structure and compound are also known as NA-831 and those terminologies are used interchangeably herein)

The present invention includes novel diketopiperazines that are structurally related to cPG.

One aspect of this invention provides novel cyclic compounds having the structural formula and substituents described below.

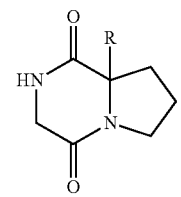

Structure 2 cyclic Glycyl-2-Allyl Proline, or
cyclic Glycyl-Alkyl Proline
(referred to herein as "cGAL")

Where R can be an Alkyl" which refers to a saturated branched, straight chain or cyclic hydrocarbon radical. Exemplary alkyl groups include methyl, ethyl, isopropyl, cyclopropyl, tort-butyl, cyclopropylmethyl, hexyl and the like. Where R can be an Ally, which refer to a group is a substituent with the structural formula. $H_2C=CH-CH_2R$, where R is the rest of the molecule. With R is a methyl, an aspect of the present invention that includes Cyclic Glycyl-2-Alkyl Proline is (8aS)-Methyl-hexahydropyrrolo[1,2-a]pyrazine-1,4-dione, which is referred to as Cyclic Glycyl-2-Methyl-Prolime or cyclicGMeP or cGMeP.

Structure 3

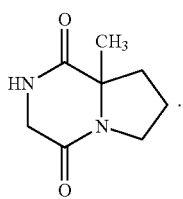

Cyclic G-2MeP
(available for purchase
from polypeptide
suppliers such as
Bachem Americas, Inc.
(Torrance, California,
USA))

In general, c(PG)3 and eGAL can be prepared by methods such as are already well-known to persons of ordinary skill in the art of peptide and modified peptide synthesis. See for example, Bodanzsky: Principles of Peptide Synthesis, Berlin, New York: Springer-Verlag 1993. Synthesis of the diketopiperazine compounds of this invention may be by solution-phase synthesis as discussed in the Examples or via the solid-phase synthesis method exemplified by Merrifield et al, 1963 *J. Amer. Chem. Soc.:* 85, 2149-2156, Specific examples of diketopiperazine synthesis can be found in Fischer, 2003, *J. Peptide Science:* 9: 9-35 and references therein. A person of ordinary skill in the art will have no difficulty, taking account of that skill and the knowledge available, and of this disclosure, in developing one or more suitable synthetic methods for compounds of this invention.

In the present application, notably but not limited to this section where compound names and structures and abbreviations are provided, the various compounds can all be used in all aspects of the present invention included herein. For example, should cPG be indicted in the specification, then all other compounds of this section (and the application as a whole) that are cPG compounds and related derivatives such as but not limited to cGAL are included in that and other descriptions, notably but not limited to methods of treatment of a variety of conditions described herein.

Structure 4

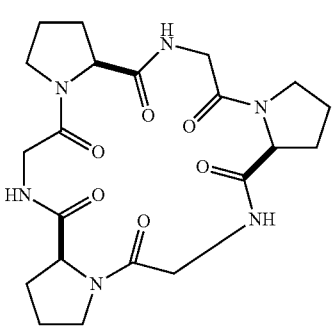

cyclic (glycyl-L-prolylglycyl-L-
prolylglycyl-L-prolyl)
(one possible structure)

The chemical synthesis of cyclic (glycyl-L-prolylglycyl-L-prolylglycyl-L-prolyl) was carried out as published in Israel Journal of Chemistry, Vol. 12, Nos. 1-2, 1974, pp. 15-29 "CYCLIC Peptides VII: The Synthesis and Characterization of Cyclic Peptides with Repeating Pro-Gly Sequences—by Charles M. Deber and Elkan R. Blout.

Synthesis of Cyc/o(glycyl-L-prolyl-glycyl-L-prolyl-glycyl-L-prolyl) A solution of p-nitrophenyl ester hydrochloride (500 mg) dissolved in dimethyl-formamide (DMF) (20 ml, dried over sodium sulfate) was added dropwise with stirring over 6 hours to 500 ml of reagent-grade pyridine, at room temperature. The bright yellow mixture was constantly stirred over 48 hours at room temperature. Solvents were removed by rotary-evaporator-high vacuum pump system at 45°. The residue was washed with 20 ml of acetone which dissolved the p-nitrophenol and pyridine hydrochloride, but left the peptidic fraction insoluble. The insoluble materials and acetone were transferred to a flask and allow acetone to evaporate at 45°. The material was then dissolved in a minimum of DMF. The white microcrystalline precipitate was shown to be Cyc/o(glycyl-L-prolyl-glycyl-L-prolyl-glycyl-L-prolyl) (155 mg, with 28% yield), formed complexed with DMF. Crystallization from methanol-ether of 100 mg of this material gave crystalline cyclo(Pro-Gly)$_3$ (55 mg) free of DMF.

Chemical analysis: Calculated for $C_{21}H_{30}N_6O_6H_2O$: C, 52.49; H, 6.71; N, 17.49. Elemental analysis found C, 52.60; H, 6.81; N, 17.38.

In still other aspects, present invention provides pharmaceutical compositions including a pharmaceutically acceptable excipient or carrier and a therapeutically effective amount of cyclic GP or its analogues with structural formulas given above to treat a disease, disorder, or condition, including but not limited to Alzheimer's disease and its related conditions such an impairment of cognitive function.

In further aspects, the present invention provides methods of treating an animal having a cognitive impairment, comprising administration to that animal an effective amount of a composition comprising cyclic GP or its analogues. In yet further aspects, the animal to be treated is a human.

One aspect of the present invention is generally directed to therapeutic treatments of neurological diseases and injuries. Expressly do not wish to be limited to any mechanisms of action, and merely propose any mechanisms of action, the inventor(s) propose that the present invention can in part be based on inducing neurogenesis, in particular, neural stem cell, or progenitor cell proliferation. In accordance with one aspect of the present invention, cyclic Prolyl Glycine and it analogues ("cPG compounds") act as key neurogenesis modulating agents that facilitate and induce proliferation and/or differentiation in neural cells.

"Neurogenesis" is defined herein as proliferation, differentiation, migration, or survival of a neural cell in vivo or in vitro. In a preferred aspect of the present invention, the neural cell can be an adult, fetal, or embryonic neural stem cell or progenitor cell. Neurogenesis also refers to a net increase in cell number or a net increase in cell survival. As used herein, "NSC" would include, at least, all brain stem cells, all brain progenitor cells, and an brain precursor cells.

It has been previously shown that increased levels of cAMP and/or $Ca^{2+}$ elicit the proliferation of adult neural stem cells. In some cases, this induction follows the activation of G-protein coupled receptors (GPCRs). Increasing intracellular cAMP and/or $Ca^{2+}$ levels through GPCR ligands can induce the increase of proliferation of adult neural stem cells.

receptors (GPCRs), also known G protein—linked receptors (GPLR), constitute a large protein family of receptors that detect molecules outside the cell and activate internal signal transduction pathways and, ultimately, cellular responses.

The ligands that bind and activate these receptors include light-sensitive compounds, odors, pheromones, hormones, and neurotransmitters, and vary in size from small molecules to peptides to large proteins. GPCRs in the mammalian brain bind several different neurotransmitters, including serotonin, dopamine, GABA, and glutamate. G protein-coupled receptors are involved in many diseases, and are also the target of approximately 34% of all modern medicinal drugs.

One aspect of the present invention includes, and not being limited by any proposed mechanisms, that cPG and its analogues can act as a neurogenesis modulating agents that modulate intracellular levels of cAMP and/or $Ca^{2+}$. cPG has been shown chemically and biologically to be capable of increasing cAMP (e.g., by increasing synthesis or decreasing breakdown) and/or $Ca^{2+}$ (e.g., by increasing influx or decreasing efflux).

One aspect of the present invention describes a new method for promoting regeneration of damaged nerve tissue, comprising administering an effective amount of cyclo Prolyl Glycine (cPG), and its analogues, which can reduce the rate of growth of glial cells to facilitate the growth of nerve tissue.

Neurons are closely surrounded by glial cells or astrocytes. One of the difficulties in achieving regeneration of neurons after they have been damaged or severed is that the glial cells proliferate and form a barrier to the regenerating neurons. The result is that the further movement of the neurons toward anticipated attachment sites is blocked and regeneration of structure and function ceases. It has been observed that formation of astrocytic and connective tissue scars and progressive necrosis have negative impact on the regeneration of neuronal functions.

Accordingly, one aspect of the present invention is a method for promoting regeneration of damaged nerve tissue in a mammal (such as a human), comprising administering an effective amount of cPG compounds (cPG and its analogues) to the damage site.

Some objectives of the experiments provided herein is to provide enablement for a method of regenerating neurons and glial cells or a method of repairing damaged neurons and glial cells as claimed.

One aspect of the invention includes, that cyclic Prolyl Glycine (cPG) and its pharmaceutically active analogues act as a neuronal modulating agents in order to treat depression and other psychological disorders. The N-methyl-D-aspartate receptor ("NMDA receptor"), is a glutamate receptor and ion channel protein found in nerve cells. The NMDA receptor is one of three types of ionotropic glutamate receptors, the others being the RMPA and kainate receptors. The NMDA receptor is activated when glutamate and glycine bind to it, and when activated it allows positively charged ions to flow through the cell membrane [Furukawa, Hiroyasu; Singh, Satinder K; Mancussol, Romina; Gouaux, Eric (November 2005). "Subunit arrangement and function in NMDA. receptors". Nature. 438 (7065): 185-92. doi: 10.1038/nature04089. PMID 16281028.].

The NMDA receptor channels play an important role in synaptic plasticity and synapse formation underlying memory, learning and formation of neural networks during development in the central nervous system (CNS). Over activation of the receptor, causing excessive influx of $Ca^{2+}$ can lead to excitotoxicity which is implied to be involved in some neurodegenerative disorders. Blocking of NMDA receptors could therefore, in theory, be useful in treating such diseases.

The NMDA receptor is an ion channel protein receptor that is activated when glycine and glutamate bind to it. The receptor is a heteromeric complex that interacts with multiple intracellular proteins by three different subunits: NR1, NR2 and NR3. NR1 has eight different subunits generated by alternative splicing from a single gene. There are four different NR2 subunits (A-D), and NR3A and NR3B subunits have been reported. Six separate genes encode for NR2 and NR3. [Loftis J. M. Janowsky A. (2003). "The N-methyl-D-aspartate receptor subunit NR2B: localization, functional properties, regulation, and clinical implications". Pharmacol Ther. 97 (1): 55-85. doi:10.1016/s0163-7258(02)00302-9.].

Agonists or allosteric modulators of NMDA receptors, in particular NR2B subunit-containing channels, have been investigated as therapeutic agents for the treatment of major depressive disorder (G. Sanacora, 2008, Nature Rev. Drug Disc. 7: 426-437). The NR2B subunit has been involved in modulating activity such as learning, memory, processing and feeding behaviors, as well as being implicated in number of human derangement. The basic structure and functions associated with the NMDA receptor can be attributed to the NR2B subunit.

An allosteric, non-competitive binding site has also been identified in the N-terminal domain of NR2B. The NR2 subunit acts as the binding site for glutamate, one of the predominant excitatory neurotransmitter receptors in the mammalian brain. [Yoshimura Y, Ohmura T, Komatsu Y (July 2003). "Two forms of synaptic plasticity with distinct dependence on age, experience, and NMDA receptor subtype in rat visual cortex". The Journal of Neuroscience. 23 (16): 6557-66. PMID 12878697].

NR2B has been associated with age- and visual-experience-dependent plasticity in the neocortex of rats, where an increased NR2B/NR2A ratio correlates directly with the stronger excitatory LTP in young animals. This is thought to contribute to experience-dependent refinement of developing cortical circuits.

The role of NR2B subunit of the NMDA receptor has been demonstrated in the action of different antidepressant agents. [Poleszak E, Wlaź P, Szewczyk B, Wláz A, Kasperek R, Wróbel A, Nowak G (2011) A complex interaction between glycine/NMDA receptors and serotonergic/noradrenergic antidepressants in the forced swim test in mice. J Neural Transm 118:1535-1546].

G-protein—coupled receptors (GPCRs), also known G protein-linked receptors (GPLR), constitute a large protein family of receptors that detect molecules outside the cell and activate internal signal transduction pathways and, ultimately, cellular responses.

GPCRs in the mammalian brain bind several different neurotransmitters, including serotonin, dopamine, GABA, and glutamate. G protein—coupled receptors are involved in many diseases and are also the target of approximately 34% of all modern medicinal drugs.

One aspect of the invention includes, that cyclic Prolyl Glycine (cPG) and its pharmaceutically active analogues act as a neuronal modulating agents in order to treat depression and other psychological disorders. One possible mechanism, though expressly not being limited to any mechanism, is the modulation of intracellular levels of cAMP and/or $Ca^{2+}$, Herein, cPG has been shown chemically and biologically to be capable of increasing cAMP (e.g., by increasing synthesis or decreasing breakdown) and: of $Ca^{2+}$ (e.g., by increasing influx or decreasing efflux).

In addition, cyclic Prolyl Glycine and its pharmaceutically active analogues have been shown to selectively bind the N-terminal domain of NR2B, which might sustain an antidepressant response in human.

The present invention provides technical advantages of cyclic Prolyl Glycine ("cPG") and its pharmaceutically active analogues, together is known as cPG compounds, which are ligands for the NR2B receptor and can be useful for the treatment of various disorders of the central nervous system. In addition, the cPG compounds provide advantages for pharmaceutical uses, for example, with regard to one or more of their mechanism of action, binding, inhibition efficacy, target selectivity, solubility, safety profiles, or bioavailability.

In carrying out the method of the invention, depressed patients are given the combination of substances at pharmaceutically effective dosage levels using appropriate routes of administration and regime. The substances can be administered in the form of a single dosage unit in which the active ingredients are combined with a suitable carrier; or they may be given in separate dosage units in which the active materials are individually combined with a suitable carrier. When administered separately, the administration may be simultaneous or at selected time intervals.

The administration is preferably orally and the carrier or carriers are selected with this in mind. While this is the case other modes of administration of both substances as well as mixed modes with the individual materials is considered part of the present invention.

The dosage levels of the materials will vary with the particular material being used and the severity of the condition of the patient being treated. The cyclic Prolyl Glycine (cPG) is used in amounts ranging from about 0.1 mg to about 10 mg per kg of body weight. It is recommended to administer orally with a dose of about 20 mg to about 80 mg per day and can be up to about 100 mg per day for some severe cases per physician's prescription order.

The pharmaceutical compositions of the present invention are prepared by utilizing the active ingredients in association with the pharmaceutical carriers conventionally employed with such materials. The compositions of the present invention are in general contemplated for administration orally to achieve an antidepressant effect. This may be in any of the dosage forms such as tablets, capsules, powders, suspensions, solutions, syrups and the like, including sustained release preparations. The term dosage form as used in this specification and the claims refer to physically discrete units to be administered in single or multiple dosage, each unit containing a predetermined quantity of active material in association with the required diluent, carrier or vehicle. The quantity of active material is that calculated to produce the desired therapeutic effect upon administration of one or more of such units.

Powders are prepared by comminuting the active substances to a suitably container size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filing operation; a glidant such as colloidal silica may be added to improve flowing properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the active substance, suitably comminuted, with a diluent or base such as starch sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets.

The medication can also be combined with free-flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral liquid formulation such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the medication in a nontoxic vehicle in which it is insoluble.

One important embodiment of the present invention, particularly for preparing solid pharmaceutical formulations, is the pharmaceutically acceptable nontoxic acid addition salts of the active drugs. Such pharmaceutically acceptable nontoxic salts include those derived from both organic and inorganic acids such as, without limitation, hydrochloric, hydrobromic, sulfuric, phosphoric, methanesulfonic, acetic, lactic, succinic, malic, maleic, aconitic, phthalic, tartaric, embonic, enenthic and the like acids.

While the present invention contemplates, primarily, oral administration, other modes are certainly not excluded. Ampules for parenteral application can be prepared and preferably contain water soluble salts of the active substances and possible buffer substances in aqueous solution.

In liquid compositions, whether designed for oral or parenteral administration in which the active substances are combined, care must be taken to insure stability of the active materials.

In cases where the active materials are to be administered separately, individual compositions are prepared in the manner indicated above. These individual compositions can then be administered as such or combined into a single-dosage unit while maintaining the separate identity, as for example in a multilayer tablet or single capsule containing both components in a plurality of discrete particles.

BRIEF DESCRIPTION OF DRAWINGS

A better understanding of the invention will be gained from reference to the following examples and drawings wherein:

FIG. 2 illustrates the proposed mechanism by which cyclic Prolyl Glycine may act to bind metal ions.

FIG. 7 Graph showing the impact of BrdU+Cells/300 micrometer at sub ventricular zone for cPG, cGMeP and c(PG)3 drug solutions.

FIG. 8 illustrates the impact of BrdU Cells/300 micrometer at dentate gyrus for cPG, c(PG)3 cGIVIel) and drug solutions.

FIG. 9 illustrates the improvement in the Ability to Concentrate and Count.

FIG. 10 illustrates the improvement in Short Term Memory.

FIG. 11 illustrates the improvement in Long Term Memory.

FIG. 12 illustrates the Impact on Orientation.

FIG. 13 illustrates the improvement in Daily Activities and Self-Care.

FIG. 14 illustrates the Impact on Emotion.

FIG. 15 illustrates the Impact of Cognitive Capacity.

The present invention is described with reference to specific embodiments thereof. Other aspects of this invention can be appreciated with reference to the drawings. Drawings have been provided in the above text and attached drawings as well, and are further provided below and their description provided at that location.

DETAILED DESCRIPTION OF THE INVENTION

The following examples are given by way of illustration only and shall not be taken as limiting the scope of the invention.

It has been surprisingly discovered that the process of the metabolism of IGF1 to the tripeptide GPE and des IGF is only a part of the process.

Figure 1:
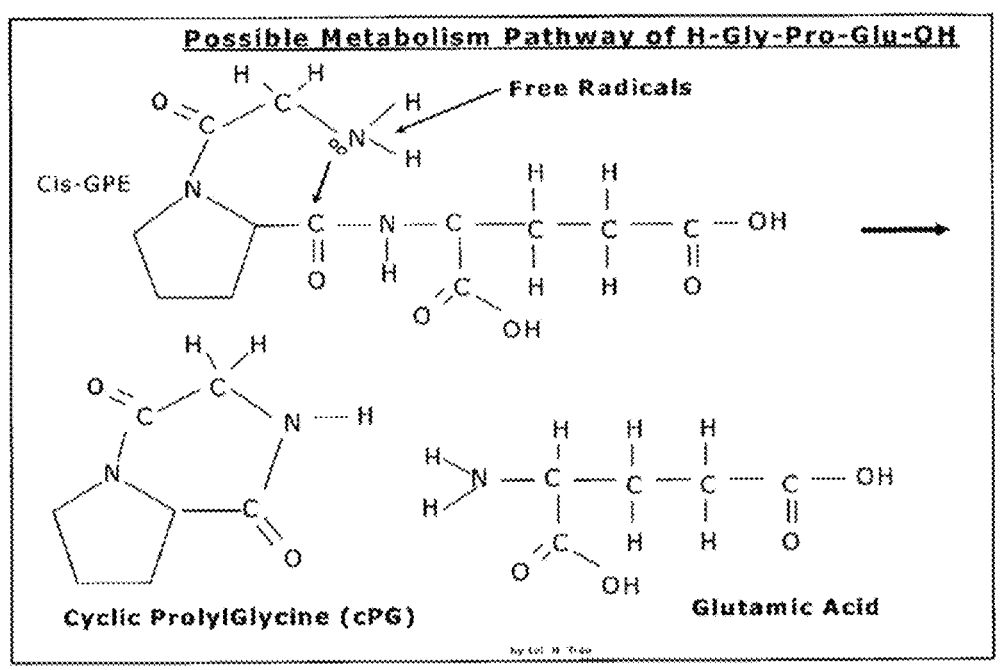
FIG. 1 illustrates the proposed metabolism pathway of cis-GPE to cyclic Prolyl Glycine and glutamic acid.

The cis-isomer of the GPE can further break down to form a cyclic Prolyl Glycine and glutamic acid. This is shown in FIG. 1.

The cyclic PG structure is sufficiently small to allow it to cross the blood-brain barrier.

Figure 2:
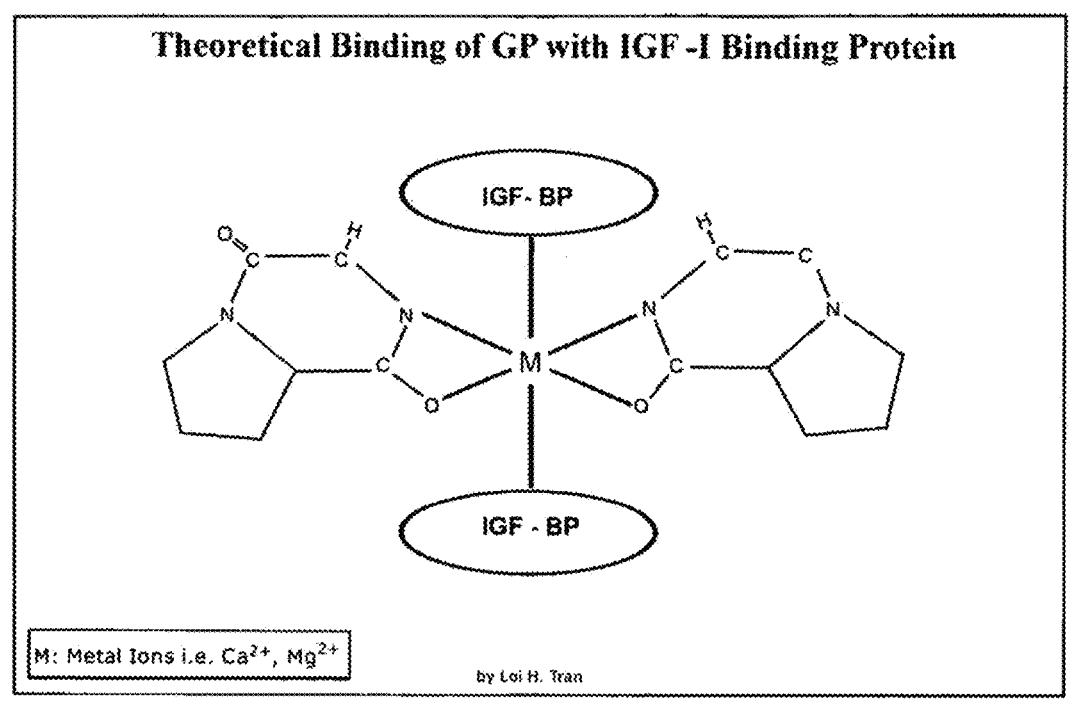

In addition, as shown in FIG. 2 the structure of the molecule is such that it is able to provide ligands for binding metal ions such as $Mg^{2+}$, $Ca^{2+}$, $Co^{2+}$ and the like and as such can act as a chelating agent.

The possible role of cPG as an agent is further supported by the companion break down product, glutamic acid.

Glutamic acid is known to be associated with brain disease. (Johnston, G. A. R. in Roberts P. J. et al Editors, Glutamate: Transmitter in the Central Nervous System, John Wiley & Sons, 1981, pp.77-8'7).

As used herein, a cPG compound is a compound with biological activity similar or identical to the biological activity of cPG; cPG compounds comprise cPG, biologically active cPG analogues, biologically active cPG mimetics, and compounds that increase the concentration of cPG and cPG analogues in a mammal. cPG compounds include cPG molecules such as truncated portions of IGF-I compounds as well as other chemical and biological analogues and mimetics.

As used herein, "cPG analogue" is any analogue of cPG, naturally occurring analogue of cPG, or any variants thereof, which are capable of effectively binding to mGluR receptors in the CNS and of promoting an equivalent neuroprotective effect on CNS nerve cells. Examples of cPG analogues are c(PG)3 and cyclic Glycyl-2-Allyl Proline, or cyclic Glycyl-Alkyl Proline or Cyclic Glycyl-2-Methyl-Proline.

The term "cPG molecules" includes peptide fragments and truncated portions of longer IGF-I compounds as well as other chemical and biological analogues and mimetics. cPG compounds can be used in the treatment of mammals, suffering from neutral injury or disease. In particular the cPG compounds can be used to treat human patients, suffering from neural injury or disease. Still more generally, the compositions and methods of the invention find use in the treatment of mammals, such as human patients, suffering from nerve damage or potential apoptotic and/or necrotic cell death, due to injuries and diseases such as septic shock, ischemia, administration of cytokines, overexpression of cytokines, ulcers, gastritis, ulcerative colitis, Crohn's disease, diabetes, rheumatoid arthritis, asthma, Alzheimer's disease, Parkinson's disease, multiple sclerosis, stroke, cirrhosis, allograft rejection, transplant rejection, encephalomyelitis, meningitis, pancreatitis, peritonitis, vasculitis, lymphocytic choriomeningitis, glomerulonephritis, uveitis, glaucoma, blepharitis, chalazion, allergic eye disease, corneal ulcer, keratitis, cataract, retinal disorders, age-related macular degeneration, optic neuritis ileitis, inflammation induced by overproduction of inflammatory cytokines, hemorrhagic shock, anaphylactic shock, burn, infection leading to the overproduction of inflammatory cytokines induced by bacteria, virus, fungus, and parasites, hemodialysis, chronic fatigue syndrome, stroke, cancers, cardiovascular diseases associated with overproduction of inflammatory cytokines, heart disease, cardiopulmonary bypass, ischemic/reperfusion injury, ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, neuroblastoma, malaria, hematologic cancers, myelofibrosis, lung injury, graft-versus-host disease, head injury, CNS trauma, hepatitis, renal failure, chronic hepatitis C, paraquat poisoning, transplant rejection and preservation, fertility enhancement, bacterial translocation, circulatory shock, traumatic shock, hemodialysis, hangover, and combinations of two or more thereof.

In addition, cPG and its analogues, such as but not limited to c(PG)3 and cGMeP can be used to treat mammals suffering from white matter insult as the result of acute brain injury, such as perinatal hypoxic-ischemic injury; or from chronic neural injury or neurodegenerative disease, such as multiple sclerosis, or from other demyelinating diseases and disorders including inflammatory involvement, such as acute disseminated encephalomyelitis, optic neuritis, transverse myelitis, Devic's disease, the leucodystrophies; non-inflammatory involvement; progressive multifocal leukoencephalopathy, central pontine myelinolysis. Patients suffering from such diseases or injuries will benefit greatly by a treatment protocol able to initiate re-myelination.

The present invention has application in the induction of myelin production following insult in the form of trauma, toxin exposure, asphyxia or hypoxia-ischemia, and has application in the treatment or prevention of apoptosis in response to injury or disease in the form of cancers, viral infections, autoimmune diseases, neurological diseases and injuries and cardiovascular diseases.

Treatment with cPG or its analogues, including but not limited to c(PG)3 and cGAL can be given before (as well as alter) an injury—as for example before elective surgery. Examples of relevant elective procedures include neural surgery, in which retraction of lobes of the brain can lead to cerebral oedema, or heart operations, such as valve replacement, in which inevitable small emboli are said to lead to detectable impairment of brain function in some 75% of cases.

Pharmacology and Utility cPG can act as an anti-necrotic and anti-apoptotic in a process of cell death. Its anti-apoptotic and anti-necrotic activity in vivo can be measured by cell counts. cPG can also be measured in vitro. (Gudasheva T. A. et al. FEBS Letters, Vol. 391, Issues 1-2, 5 Aug. 1996, pp. 149-152). CNS damage may for example be measured clinically by the degree of permanent neurological deficit cognitive function, and/or propensity to seizure disorders. (Rakic L. J et al, in Rakic L. J et al Peptide and Amino Acid Transport Mechanisms in The Central Nervous System, 1988, The MacMillan Press Ltd. (London) pp.167-181).

Pharmaceutical Compositions and Administration cPG itself as part of the present invention can be used to prevent or treat cell damage and programmed death and the induction of myelin production. Usually this is effected through the direct administration of cGP to the patient. If desired, a combination of the cPG compounds and its analogues can be administered in a pharmaceutically acceptable composition.

Those skilled in the art will appreciate there is no intention on the part of the applicants to exclude administration of other forms of cPG and its analogues. By way of example, the effective amount of cPG in the CNS can be increased by administration of a pro-drug from of cPG, which comprises cPG and a carrier, cPG and the carrier being joined by a linkage which is susceptible to cleavage or digested within the patient. Any suitable linkage can be employed which will be cleaved or digested to release cPG following administration.

In addition, it is envisaged cPG levels may be increased through an implant that includes a cell line capable of expressing cPG in an active from within the CNS of the patient.

Pro-drugs of cPG and its analogues can also be administered. In that instance, the pro-drug is metabolized or otherwise altered within the subject to form cPG. cPG and its analogues, such as but not limited to c(PG)3 and cyclic Glycyl-2-Allyl Proline, or cyclic Glycyl-Alkyl Proline or Cyclic Glycyl-2-Methyl-Prolime can be administered as part of a medicament or pharmaceutical preparation. This can involve combining cPG with any pharmaceutically appropriate carrier, adjuvant or excipient. The selection of the carrier, adjuvant or excipient will of course usually be dependent upon the route of administration to be employed.

The administration route can vary widely and be any appropriate route of administration. An advantage of cPG is that it can be administered peripherally. This means it need not be administered directly to the CNS of the patient in order to have effect in the CNS.

Any peripheral route known in the art can be employed. These can include but are not limited to parenteral routes for example injection into the peripheral circulation, subcutaneous, intraorbital, ophthalmic, intraspinal, intracisternal, topical, infusion (using e.g., controlled release devices or minipumps such as osmotic pumps or skin patches), implant, aerosol, inhalation, scarification, intraperitoneal, intracapsular, intramuscular, intranasal, oral, buccal, pulmonary, rectal or vaginal. The compositions can be formulated for parenteral administration to humans or other mammals in therapeutically effective amounts (e.g., amounts which eliminate or reduce the patient's pathological condition) to provide therapy for the neurological diseases described above.

Two of the preferred administration routes will be by subcutaneous injection (such as but not limited to, dissolved in 0.9% sodium chloride) or orally (in a capsule).

It will also be appreciated that on occasion it may desirable to directly administer cPG compounds to the CNS of the patient. Again, this can be achieved by any appropriate direct administration route. Examples include administration by lateral cerebroventricular injection or through a surgically inserted shunt into the lateral cerebroventricle of the brain of the patient.

The calculation of the effective amount of cPG compounds to be administered is within the skill of one of ordinary skill in the art, and will be routine to those persons skilled in the art. Needless to say, the final amount to be administered will be dependent upon the route of administration and upon the nature of the neurological disorder or condition that is to be treated. Preferably the cPG compound will be administered at between about 1 μg to 100 mg of cPG compound per per kilogram of body weight where the dose is administered centrally. A suitable dosage for administration of cPG may be, for example, at between about 0.1 mg to about 10 mg per per kilogram of body weight, or at between about 1 mg to about 5 mg per per kilogram body weight.

For inclusion in a medicament, cPG compounds can be obtained from a suitable commercial source such as Bachem A G of Bubendorf, Switzerland. Alternatively, cPG can be directly synthesized by conventional methods such as the stepwise solid phase synthesis method of Merrifield et al. 1963 J. Amer. Chem. Soc.: 85, 2149-2156. Alternatively synthesis can involve in the use of commercially available peptide synthesizers such as the Applied Biosystems model 430A.

cGAL can be prepared by methods such as are well-known to those of ordinary skill in the art of the synthesis of peptides and analogues. Example: "Principles of Peptide Synthesis" by Bodanzsky, published by Springer-Verlag 1993.

c(PG)3 can be prepared by the method published in the Israel Journal of Chemistry, Vol. 12, Nos. 1-2, 1974, pp. 15-29 "CYCLIC Peptides VII: The Synthesis and Characterization of Cyclic Peptides with Repeating Pro-Gly Sequences—by Charles M. Deber and Elkan R. Blout.pu.

As a general proposition, the total pharmaceutically effective amount of the cPG compound administered parenterally per dose will be in a range that can be measured by a dose response curve. One can administer increasing amounts of the cPG compound to the patient and check the serum levels of the patient for cPG. The amount of cPG compound to be employed can be calculated on a molar basis based on these serum levels of cPG.

Specifically, one method for determining appropriate dosing of the compound entails measuring cPG levels in a biological fluid such as a body or blood fluid. Measuring such levels can be done by any means, including RIA and ELISA. After measuring cPG levels, the fluid is contacted with the compound using single or multiple doses. After this contacting step, the cPG levels are re-measured in the fluid. If the fluid cPG levels have fallen by an amount sufficient to produce the desired efficacy for which the molecule is to be administered, then the dose of the molecule can be adjusted to produce maximal efficacy. This method can be carried out in vitro or in vivo. Preferably, this method is carried out in vivo, i.e., after the fluid is extracted from a mammal and the cPG levels measured, the compound herein is administered to the mammal using single or multiple doses (that is, the contacting step is achieved by administration to a mammal) and then the cPG levels are remeasured from fluid extracted from the mammal.

The compound may also be suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al, 1981), ethylene vinyl acetate (Langer et al., supra), or poly-D-(−)-3-hydroxybutyric acid (EP 133,988). Sustained-release compositions also include a liposomally entrapped compound. Liposomes containing the compound are prepared by methods known per se: DE Patent 3,218,121; Epstein et al., 1985; Hwang et al., 1980; EP Patent 52,322; EP Patent 36,676; EP Patent 88,046; EP Patent 143,949; EP Patent 142,641; Japanese Pat. Appin. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy.

PEGylated peptides having a longer life can also be employed, based on, e.g., the conjugate technology described in WO 95/32003, published Nov. 30, 1995.

If parenteral administration is preferred, the compound is formulated generally by mixing each at the desired concentration, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation.

Generally, the formulations are prepared by contacting the compound with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate may also be used.

The carrier may additionally contain additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrin; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$ $CaCl_2$ etc.

The cPG compound is typically formulated in such vehicles at a pH of between about 5.5 to about 8.0. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent, and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

The compound to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The compound ordinarily will be stored in unit or multi-dose containers, for example, sealed glass ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Combination therapy with the cPG compound herein and one or more other appropriate reagents that increase total cPG in the blood or enhance the effect of the cPG is also contemplated. These reagents generally allow the cPG compound herein to release the generated cPG.

In addition, one aspect of the present invention includes using gene therapy for treating a mammal, using nucleic acid encoding the cPG compound, if it is a peptide. Generally, gene therapy is used to increase (or overexpress) cPG levels in the mammal. Nucleic acids, which encode the cPG peptide can be used for this purpose. Once the amino acid sequence is known, one can generate several nucleic acid molecules using the degeneracy of the genetic code, and select which to use for gene therapy.

There are two major approaches to getting the nucleic acid (optionally contained in a vector) into the patient's cells for purposes of gene therapy: in vivo and ex vivo. For in vivo delivery, the nucleic acid is injected directly into the patient, usually at the site where the cPG compound is required. For ex vivo treatment, the patient's cells are removed, the nucleic acid is introduced into these isolated cells, and the modified cells are administered to the patient either directly or, for example, encapsulated within porous membranes which are implanted into the patient. See, e.g., U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell-surface membrane protein or the target cell, a ligand for a receptor on the target cell, etc. Where liposomes are employed, proteins which bind to a cell-surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., 1987; Wagner et al., 1990). For review of the currently known gene marking and gene therapy protocols, see Anderson 1992. See also WO 93/25673 and the references cited therein.

Kits are also contemplated for this invention. A typical kit would comprise a container, preferably a vial, for the cPG compound formulation comprising cPG compound in a pharmaceutically acceptable buffer and instructions, such as a product insert or label, directing the user to utilize the pharmaceutical formulation.

Certain aspects of the present invention include the use of cPG in treatment of cognitive impairment associated with aging with neurodegenerative conditions or in situations in which cognitive impairment is found with no apparent neurodegeneration.

Such other agents can be selected from the non-limiting group of, for example, growth factors and associated derivatives, e.g., insulin-like growth factor-I (IGF-I), insulin-like growth factor-II (IGF-II), growth hormone, nerve growth factor, growth hormone binding protein, and/or IGF-binding proteins.

Therapeutic Applications

Compositions and methods of the present invention find use in the treatment of animals, such as human patients, suffering from cognitive impairment. Still more generally, the compositions and methods of the invention find use in the treatment of mammals, such as but not limited human patients and subjects, suffering from memory impairment, mild cognitive impairment, dementia, including dementia including dementias resulting from cerebral atrophy associated with Alzheimer's disease, Lewy-bodies disease, frontotemporal lobar degeneration, vascular dementia, head trauma; Huntington's disease, Parkinson's disease, or Down's syndrome.

Pharmaceutical Compositions and Administration

Cyclic PG compounds can be administered as part of a medicament or pharmaceutical preparation. This can involve combining a compound of the invention with any pharmaceutically appropriate carrier, adjuvant or excipient. The selection of the carrier, adjuvant or excipient will of course usually be dependent upon the route of administration to be employed.

In general, compounds of the present invention will be administered in therapeutically effective amounts by any of the usual modes known in the art, either singly or in combination with other conventional therapeutic agents for the disease being treated. A therapeutically effective amount may vary depending on the disease or injury, its severity, the age and relative health of the animal being treated, the potency of the compound(s), and other factors. Therapeutically effective amounts of cyclic Prolyl Glycine can range from 0.01 to 10 milligrams per kilogram mass of the animal, with lower doses such as 0.01 to 0.1 mg/kg being appropriate for administration through the cerebrospinal fluid, such as by intracerebroventricular administration, and higher doses such as 0.1 to 10 mg/kg being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

Cyclic Prolyl Glycine and cPG compound can be administered orally or peripherally via any peripheral route known in the art. These can include but are not limited to parenteral routes for example injection into the peripheral circulation, subcutaneous, intraorbital, ophthalmic, intraspinal, intracisternal, topical, intravenous infusion, aerosol, inhalation, scarification, intraperitoneal, intracapsular, intramuscular, intranasal, buccal, transdermal, pulmonary, rectal or vaginal.

For the convenience to the patients, the cyclic Prolyl Glycine and cPG compounds can be administered orally. The amount of a compound of this invention in the composition may vary widely depending on the type of composition, size of a unit dosage, kind of excipients, and other factors well known to those of ordinary skill in the art. In general, the final composition may comprise from 5 mg to 50 mg of cPG for a typical adult weighing 50 to 120 kg or $1 \times 10^{-5}$ percent to $3 \times 10^{-4}$ by weight (% w) with the remainder being the excipient or excipients.

Other convenient administration routes include subcutaneous injection or intravenous infusion (for example the active cPG is dissolved in a physiologically compatible carrier such as 0.9% sodium chloride or dextrose) or direct administration to the CNS. Using stereotactic devices and accurate maps of an animals' CNS, a compound can be injected directly into a site of neural damage.

The effective amount of compound in the CNS can be increased by administration of a pro-drug form of a compound, which comprises a compound of the invention and a carrier, where the carrier is joined to a compound of the invention by a linkage which is susceptible to cleavage or digestion within the patient. Any suitable linkage can be employed which will be cleaved or digested following administration.

However, there is no intention on the part of the applicants to exclude other forms of administration.

In other embodiments of the present invention, restoring nerve function in an animal can include administering a therapeutic amount of cyclic Prolyl Glycine or cPG compounds in combination with another neuroprotective agent, selected from, for example, growth factors and associated derivatives (insulin-like growth factor-I (IGF-I), insulin-like growth factor-II (IGF-II), transforming growth factor-β1, activin, growth hormone, nerve growth factor, growth hormone binding protein, IGF-binding proteins, keratinocyte growth factor, androgen-induced growth factor. Additional members of the FGF family include, for example, fibroblast growth factor homologous factor-1 (FHF-1), FHF-2, FHF-3 and FHF-4, karatinocyte growth factor 2, brain derived growth factor, neurotrophin 3, and neurotrophin 4. Other forms of neuroprotective therapeutic agents include clomethiazole, kynurenic acid, Semax, tacrolimus; glutamate agonist such as, NPS1506, GV1505260, MK-801, GV150526; AMPA ants such as 2,3-dihydroxy-6-nitro-7-sulfamoylbenzo(f)quinoxaline (NBQX); anti-inflammatory agents directed against the addressin MAdCAM-1 and/or its integrin α4 receptors (α4β1 and α4β7), such as anti-MAdCAM-1mAb MECA-367 (ATCC accession no. HB-9478).

Cyclic Prolyl Glycine compounds can be suitably administered by a sustained-release system. Suitable examples of sustained-release compositions include semi-permeable polymer matrices in the form of shaped articles, for example, films, or microcapsules.

For parenteral administration, in one embodiment cyclic Prolyl Glcyine or cPG compounds is formulated generally by mixing each at the desired degree of purity, in a unit dosage injectable form (solution, suspension, or emulsion), with a pharmaceutically, or parenterally, acceptable carrier, for example, one that is non-toxic to recipients at the dosages and concentrations employed and is compatible with other ingredients of the formulation.

Generally, the formulations are prepared by contacting cyclic Prolyl Glycine or cPG compounds uniformly and intimately with liquid carriers or finely divided solid carriers or both. Then, if necessary, the product is shaped into the desired formulation. Preferably the carrier is a parenteral carrier, ore preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

Cyclic Prolyl Glycine or cPG compounds are typically formulated in such vehicles at a pH of from or about 4.5 to 8. It will be understood that use of certain of the foregoing excipients, carriers, or stabilizers will result in the formation of salts of the compound. The final preparation may be a stable liquid or lyophilized solid.

Formulations of cyclic Prolyl Glycine or cPG compounds in pharmaceutical compositions can also include adjuvants. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavouring agent such as peppermint, wintergreen, or cherry. When dosage forms are tablets, cyclic Prolyl Glycine or a cPG compounds and compositions can include binders and optionally, a smooth coating. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a colouring agent, and a flavouring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired.

For injection, intraventricular administration and other invasive routes of administration, cyclic Prolyl Glycine or cPG compounds are preferably sterile. Sterility may be accomplished by any method known in the art, for example filtration through sterile filtration membranes (for example, 0.2-micron membranes). Therapeutic compositions generally are placed into a container having a sterile access port, for example, an intravenous solution bag or vial having a stopper able to be pierced by a hypodermic injection needle.

Preferred Aspects of the Present Invention

A first aspect of the present invention includes a method of regenerating neurons and glia cell loss as a result of an insult from injury or disease, including the steps of: a) providing a subject in need of said regenerating neurons and glia cell loss; and b) administering to the subject cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, in an effective amount to regenerate new neurons and glia; wherein the neurons are regenerated and the glia cell loss is regenerated in said subject; further wherein the cPG compound serves as a neurogenesis agent in the central nervous system; and further wherein the neurons and glia cell loss as a result of an insult from injury or disease are regenerated.

Regenerating neurons generally refers to the regrowth or repair of neurons, glia, axons, myelin, or synapses. Researchers are developing new tools to effectively control the process of neural injury and degeneration and to create a microenvironment that enhances the capacity for innate repair and the efficacy of other regeneration strategies, including neural cell replacement and neurorehabilitation. Experiment 7 and Experiment 8 describe the method of regenerating neurons and glia cell loss as a result of an insult from injury or disease Another aspect of the present invention includes wherein the administration is in the form of a pharmaceutical composition including a pharmaceutically acceptable carrier.

A further aspect of the present invention includes wherein the effective amount of cPG compound is from about 1 μg to about 100 mg per kg of body weight.

An additional aspect of the present invention includes wherein the administration is in combination with artificial cerebrospinal fluid.

Another aspect of the present invention includes wherein the administration is intravenous.

A further aspect of the present invention includes wherein the administration is combined with a neuroprotective agent, insulin-like growth factor-I (IGF-I) or insulin growth-like factor-II (IGF-II).

An additional aspect of the present invention wherein the administration is combined with an anti-inflammatory agent, anti-integrin alpha 4 subunit reagents.

A second aspect of the present invention includes a method of repairing damaged neurons and glia cell loss as a result of an insult from injury or disease, including the step of: a) providing a subject in need of said regenerating neurons and glia cell loss; and b) administering to the subject cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, in an effective amount to regenerate new neurons and glia; wherein the neurons are regenerated and the glia cell loss is regenerated in said subject; wherein said cPG serves as a neurorescue agent in the central nervous system and further wherein the damaged neurons and glia cell loss as a result of an insult from injury or disease are repaired.

Repairing damaged neurons generally refers to reconstructive techniques or processes to repair damaged neurons to prevent neuronal and glial loss. The present invention describes methods that can repair damaged neurons and glia following traumatic, anoxic, infectious, and immunological adverse effects. The old doctrine that axons cannot be made to regenerate, and dead neurons cannot be replaced, is no longer tenable. In particular, Experiment 7 and Experiment 8 describe the repairing process through neuronal, glial, and pharmacological interventions.

Another aspect of the present invention includes wherein cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, is from about 1 µg to about 100 mg per kg of body weight.

A further aspect of the present invention includes wherein the administration is in the form of a pharmaceutical composition including pharmaceutically acceptable carrier thereof.

An additional aspect of the present invention includes wherein the administration is in combination with artificial cerebrospinal fluid.

Another aspect of the present invention includes wherein the administration is combined with a neuroprotective agent, insulin-like growth factor-I (IGF-I) or insulin growth-like factor-II (IGF-II).

A further aspect of the present invention includes herein the administration is combined with an anti-inflammatory agent.

A third aspect of the present invention includes a method for relieving or alleviating of cognitive impairment caused by a disease, injury, or condition in a mammal in need thereof, comprising: a) providing a mammal in need of relieving or alleviating of cognitive impairment caused by a disease, injury, or condition; and b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to said mammal; wherein the disease is selected from the group consisting of Alzheimer's disease, Huntington's disease, Lewy Body disease, Dementia, and multi-infarct dementia, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration; further wherein the injury is selected from the group consisting of neurotoxic injury, cerebral hypoxia/ischemia, traumatic brain injury, coronary artery bypass surgery, where said condition is normal aging, age-related memory loss, memory impairment, cholinergic hypofunction, vascular narrowing or blockage in the brain, neuroinflammation, mild cognitive impairment, cerebral atrophy, frontotemporal lobar degeneration, Pick's disease, HIV infection, Down's syndrome, and loss of synaptic plasticity; further wherein said mammal is for relieved or alleviated of cognitive impairment caused by a disease, injury, or condition, including Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

Relieving cognitive impairment generally refers to methods that can relieve symptoms related to memory, thinking, language and other thought processes. In addition, they may also help with mood, agitation and other behavioral issues.

Another aspect of the present invention includes wherein said cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, includes an aqueous solution and one or more pharmaceutically acceptable excipients, additives, carriers or adjuvants.

A further aspect of the present invention includes wherein said cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, further includes one or more excipients, carriers, additives, adjuvants or binders in a tablet or capsule.

An additional aspect of the present invention includes wherein the disorder is a mild cognitive impairment, Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

Another aspect of the present invention includes wherein the cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, vaginal, or a combination thereof, route of administration.

Another aspect of the present invention includes wherein the pharmaceutically effective amount has a lower limit of about 0.001 milligrams per kilogram mass (mg/kg) of said mammal and an upper limit of about 100 mg/kg of said mammal.

A further aspect of the present invention includes wherein the cognitive impairment is caused by cholinergic hypofunction.

An additional aspect of the present invention includes wherein the cognitive impairment is caused by a decrease in glutamate receptors in the granular cell layer (CA1) of the hippocampus of said mammal.

Another aspect of the present invention includes wherein the cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, causes an increase in AMPA receptors in the granular cell layer (CA1) of the hippocampus of said mammal.

A further aspect of the present invention includes wherein the cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, causes an increase in neuronal plasticity caused by said cPG compound in the granule cell layer (CA1) and the pyramidal cell layer (CA3) regions of said mammal's hippocampus.

An additional aspect of the present invention includes wherein the cerebral hypoxia/ischemia caused by traumatic brain injury.

Another aspect of the present invention includes wherein the cognitive impairment caused by multi-infarct dementia.

A further aspect of the present invention includes wherein the cognitive impairment caused by coronary arterial bypass surgery (CABG).

An additional aspect of the present invention includes wherein the cognitive impairment caused by Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

A fourth aspect of the present invention includes a method of preventing the symptoms of a mild cognitive impairment caused by or associated with a disease, injury, or condition in a mammal in need thereof, including: a) providing a mammal in need of preventing cognitive impairment caused by a disease, injury, or condition; b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the mammal; wherein the disease is selected from the group consisting of Alzheimer's disease, Huntington's disease, Lewy Body disease, Dementia, and multi-infarct dementia, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

Preventing the symptoms of a mild cognitive impairment generally refers actions that would be performed to prevent the symptomatic phase and primarily to reduce the risk of disease. Typically, prevention in dementia can be referred to as levels of prevention: primary, secondary and tertiary.

In degenerative dementias, the secondary prevention stage can apply to the phase of mild cognitive impairment. At this point, symptoms are present but are not sufficiently severe to constitute dementia. Therefore, treatment of cPG compounds aimed at subjects with MCI could be considered secondary prevention studies.

Tertiary prevention refers to a treatment designed to halt the progression of the disease once it has been established. The goal is to reduce the disability and improve the long-term prognosis for individuals with the mild cognitive impairment.

A fifth aspect of the present invention includes a method of treating the symptoms of a mild cognitive impairment caused by or associated with a disease, injury, or condition in a mammal in need thereof, including: a) providing a mammal in need of treating of cognitive impairment caused by a disease, injury, or condition; b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the mammal; wherein the disease is selected from the group consisting of Alzheimer's disease, Huntington's disease, Lewy Body disease, Dementia, and multi-infarct dementia, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

Treating the symptoms of a mild cognitive impairment generally refers to treating cognitive function, or the process of thought, includes but is not limited to abilities such as learning, reading, speaking and writing. Patients with mild cognitive impairment (MCI) retain these important cognitive skills, necessary to manage their everyday activities, but have difficulty remembering recent events or recently acquired information. Long-term memories tend to remain intact. In particular, see Experiment 12, Clinical Trial on Alzheimer's Patients with Mild Cognitive Impairment.

Neurons, are among the most ancient of all specialized animal cell types. Their structure is like that of no other class of cells. The central challenge of neural growth development is how to cause axons and dendrites grow out, find their right partners, and synapse with them selectively to create a functional network.

A sixth aspect of the present invention includes a method of increasing neuronal growth or synapse formation in a mammal caused by or associated with a disease, injury, or condition in a mammal in need thereof including: a) providing a mammal in need of increasing neuronal growth or synapse formation; b) administering an effective amount of a composition that comprising a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG, or a combination thereof, to the mammal; wherein the disease is selected from the group consisting of Alzheimer's disease, Huntington's disease, Lewy Body disease, Dementia, and multi-infarct dementia, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration A seventh aspect of the present invention includes a method for relieving or alleviating of cognitive impairment caused by a disease, injury, or condition in a mammal in need thereof, including: a) providing a mammal in need of relieving or alleviating of cognitive impairment caused by a disease, injury, or condition; and b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the mammal; wherein the disease is selected from the group consisting of Alzheimer's disease, Huntington's disease, Lewy Body disease, Dementia, and multi-infarct dementia, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration; further wherein the injury is selected from the group consisting of neurotoxic injury, cerebral hypoxia/ischemia, traumatic brain injury, coronary artery bypass surgery, where said condition is normal aging, age-related memory loss, memory impairment, cholinergic hypofunction, vascular narrowing or blockage in the brain, neuroinflammation, mild cognitive impairment, cerebral atrophy, frontotemporal lobar degeneration, Pick's disease, HIV infection, Down's syndrome, and loss of synaptic plasticity; further wherein said mammal is for relieved or alleviated of cognitive impairment caused by a disease, injury, or condition, including Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

Another aspect of the present invention includes wherein the cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, comprises an aqueous solution and one or more pharmaceutically acceptable excipients, additives, carriers or adjuvants.

A further aspect of the present invention includes wherein the cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, further comprises one or more excipients, carriers, additives, adjuvants or binders in a tablet or capsule.

An additional aspect of the present invention includes wherein the disorder is a mild cognitive impairment, Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

Another aspect of the present invention includes wherein the cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, vaginal, or a combination thereof, route of administration.

A further aspect of the present invention includes wherein the pharmaceutically effective amount has a lower limit of about 0.001 milligrams per kilogram mass (mg/kg) of said mammal and an upper limit of about 100 mg/kg of said mammal.

An additional aspect of the present invention includes wherein the cognitive impairment is caused by cholinergic hypofunction.

Another aspect of the present invention includes wherein the cholinergic hypofunction is caused by scopolamine.

A further aspect of the present invention includes wherein the cognitive impairment is age-related memory loss, cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

An additional aspect of the present invention includes wherein the cognitive impairment is caused by a decrease in glutamate receptors in the granular cell layer (CA1) of the hippocampus of said mammal.

Another aspect of the present invention includes wherein the cPG compound causes an increase in AMPA receptors in the granular cell layer (CA1) of the hippocampus of said mammal.

A further aspect of the present invention includes wherein the cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, causes an increase in neuronal plasticity caused by said cPG compound in the granule cell layer (CA1) and the pyramidal cell layer (CA3) regions of said mammal's hippocampus.

An additional aspect of the present invention includes wherein the cerebral hypoxia/ischemia caused by traumatic brain injury.

Another aspect of the present invention includes wherein the cognitive impairment caused by multi-infarct dementia.

A further aspect of the present invention includes wherein the cognitive impairment caused by coronary arterial bypass surgery (CABG).

An additional aspect of the present invention includes wherein the cognitive impairment caused by Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

An eight aspect of the present invention includes a method of preventing the symptoms of a mild cognitive impairment caused by or associated with a disease, injury, or condition in a mammal in need thereof, including: a) providing a mammal in need of preventing cognitive impairment caused by a disease, injury, or condition; and b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG, or a combination thereof, to the mammal; wherein the disease is selected from the group consisting of Alzheimer's disease, Huntington's disease, Lewy Body disease, Dementia, and multi-infarct dementia, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

A ninth aspect of the present invention includes a method of treating the symptoms of a mild cognitive impairment caused by or associated with a disease, injury, or condition in a mammal in need thereof, including: a) providing a mammal in need of treating of cognitive impairment caused by a disease, injury, or condition; and b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the mammal; wherein the disease is selected from the group consisting of Alzheimer's disease, Huntington's disease, Lewy Body disease, Dementia, and multi-infarct dementia, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

A tenth aspect of the present invention includes a method of increasing neuronal growth or synapse formation in a mammal caused by or associated with a disease, injury, or condition in a mammal in need thereof including: a) providing a mammal in need of increasing neuronal growth or synapse formation; and b) administering an effective amount of a composition that comprising a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the mammal; wherein the disease is selected from the group consisting of Alzheimer's disease, Huntington's disease, Lewy Body disease, Dementia, and multi-infarct dementia, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

An eleventh aspect of the present invention includes a method for modulating neurogenesis in neural tissue of a patient exhibiting at least one symptom of a central nervous system disorder that is neurodegenerative disorders, ischemic disorders, neurological traumas, learning and memory disorders, or a combination thereof, by administrating cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, or its functional or active analogs, variants, derivatives, that have the same, substantially the same, or similar function as cPG, and combinations thereof, wherein the agent modulates neurogenesis in the patient, thereby modulating neurogenesis in the neural tissue of the patient.

Neurogenesis is the process by which new neurons arise from neural stem and progenitor cells, mature, specialize and become integrated and functional within the neuronal network. Modulating neurogenesis in neural tissue generally refers to method to exert a modifying or controlling influence on the neuronal growth in the human brain.

Another aspect of the present invention includes wherein the nervous system disorder is Alzheimer's disease, Parkinson's disease and Parkinsonian disorders, Huntington's disease multiple sclerosis, amyotrophic lateral sclerosis, Shy-Drager syndrome, progressive supranuclear palsy, Lewy body disease, spinal ischemia, ischemic stroke, cerebral infarction, spinal cord injury, and cancer-related brain and spinal cord injury, multi-infarct dementia, geriatric dementia, mild cognition impairment, depression and traumatic injury.

A further aspect of the present invention includes wherein the modulating neurogenesis is performed by an activation of a GPCR receptor in said neural tissue.

An additional aspect of the present invention includes wherein the agent is administered at an amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, from about 0.1 mg to about 10 mg/kg per day, from about 0.5 mg to about 20 mg/kg per day, from about 0.2 mg to about 40 mg/kg per day, from about 5 mg to about 50 mg/kg per day, or from about 10 micrograms to about 100 mg/kg per day.

An twelfth aspect of the present invention includes a method for modulating neurogenesis in neural tissue of a patient exhibiting at least one symptom of a central nervous system disorder that is neurodegenerative disorders, ischemic disorders, neurological traumas, learning and memory disorders, or a combination thereof, by administrating said patient an amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, sufficient to increase adult neural stem cells in said patient and reduce at least one symptom of said disorder.

Another aspect of the present invention includes wherein the disorder is, Alzheimer's disease, Parkinson's disease and Parkinsonian disorders, Huntington's disease multiple sclerosis, amyotrophic lateral sclerosis, Shy-Drager syndrome, progressive supranuclear palsy, Lewy body disease, spinal ischemia, ischemic stroke, cerebral infarction, spinal cord injury, and cancer-related brain and spinal cord injury, multi-infarct dementia, geriatric dementia, cognition impairment, depression, traumatic injury, or a combination thereof.

Another aspect of the present invention includes wherein the cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, is administered from about 0.01 mg/kg to about 100 mg per kilogram of body weight per day.

A thirteenth aspect of the present invention includes a method for treating depression or other psychological disorder in a subject, including: a) providing a subject in need of treatment of depression or other psychological disorders; and b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the subject; wherein the subject is treated for depression or other psychological disorders.

Depression symptoms can vary from mild to severe and can include: feeling sad or having a depressed mood, loss of interest or pleasure in activities once enjoyed, changes in appetite—weight loss or gain unrelated to dieting, trouble sleeping or sleeping too much, loss of energy or increased fatigue, difficulty thinking, concentrating or making decisions, and thoughts of death or suicide.

Another aspect of the present invention includes wherein the cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, comprises an aqueous solution and one or more pharmaceutically acceptable excipients, additives, carriers or adjuvants.

A further aspect of the present invention includes wherein the cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, further comprises one or more excipients, carriers, additives, adjuvants or binders in a tablet or capsule.

An additional aspect of the present invention includes wherein the cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, vaginal, or a combination thereof, route of administration.

Another aspect of the present invention includes wherein the pharmaceutically effective amount has a lower limit of about 0.1 milligrams per kilogram mass (mg/kg) of said mammal and an upper limit of about 10 mg/kg of said mammal.

A further aspect of the present invention includes wherein the pharmaceutically effective amount is between about 20 mg and about 80 mg per day given orally and can be up to 100 mg per day for some severe cases per physician's prescription order.

A thirteenth aspect of the present invention includes a method of preventing the symptoms of depression or other psychological disorders in subject in need thereof, including: a) providing a subject in need of preventing depression or other psychological disorders; b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the subject; wherein the subject is prevented from developing the symptoms of depression or other psychological disorders.

Preventing the symptoms of depression generally refers to the prevention of medical illness that negatively affects how the person feels, thinks and acts. Depression causes feelings of sadness and/or a loss of interest in activities once enjoyed. It can lead to a variety of emotional and physical problems and can decrease a person's ability to function at work and at home. In particular, see Experiment 15.

A fourteenth aspect of the present invention includes a method of treating the symptoms of depression or other psychological disorders in a subject in need thereof, including: a) providing a subject in need of treating of depression or other psychological disorders; b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the mammal; wherein the subject is treated for the symptoms of depression or other psychological disorders.

Depression symptoms can vary from mild to severe and can include: feeling sad or having a depressed mood, loss of interest or pleasure in activities once enjoyed, changes in appetite weight loss or gain unrelated to dieting, trouble sleeping or sleeping too much, loss of energy or increased fatigue, difficulty thinking, concentrating or making decisions, and thoughts of death or suicide.

A fifteenth aspect of the present invention includes a method for the treatment of mentally depressed patients, including: a) providing a subject in need of treating of depression or other psychological disorders; b) administering to a patient suffering from mental depression a pharmaceutically effective amount (such as but not limited to from 20 mg to 80 mg per day) of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, wherein the subject is treated for mental depression.

Treating of mentally depressed patients has generally referred to using antidepressants available in the market which normally increase the risk of suicidal thoughts and behavior in children, adolescents, and young adults in short-term studies. In the present invention, cPG has been demonstrated to serve as an effective an antidepressant with little or no adverse effects, see Experiment 15.

A sixteenth aspect of the present invention includes a method for relieving or alleviating the the symptoms of depression or other psychological disorders in a subject in need thereof, including: a) providing a subject in need of relieving or alleviating depression or other psychological disorders; b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the mammal; wherein the subject is alleviated for the symptoms of depression or other psychological disorders.

A seventeenth aspect of the present invention includes a method for intervening or prevention the cascade of depression or other psychological disorders in a subject in need thereof, including: a) providing a subject in need of intervention or prevention of depression or other psychological disorders; b) administering a pharmaceutically effective amount of cyclic Prolyl Glycine (cPG) or its analogues (cyclic(tri(Prolyl Glycine) or cyclic Glycyl-2-Allyl Proline, or cyclic Glycyl-Alkyl Proline or cyclic Glycyl-2-Methyl-Proline (cPMeG), collectively called a cPG compound, or a combination thereof, to the mammal; wherein said the subject is prevented for the symptoms of depression or other psychological disorders.

While well-established treatments exist for depression, estimates suggest a majority of persons with depression do not receive appropriate care. The timely intervention is an important element of the continuum of care model to person with Major Depressive Episodes. In particular, see Experiment 15.

EXAMPLES

The following in vitro and in-vivo studies demonstrate efficacy of cyclic Prolyl Glycine in reducing cognitive impairment. They are not intended to be limiting, and other compositions and methods of this invention can be developed without undue experimentation. All the following experiments were carried out using protocols developed under guidelines approved by the Animal Ethics Committee and Institutional Review Board.

Cyclic Prolyl Glycine is available from commercial suppliers such as Bachem (Torrance, Calif.), and Sigma (St. Louis, Mo.), Experiment 1

Figure 3:
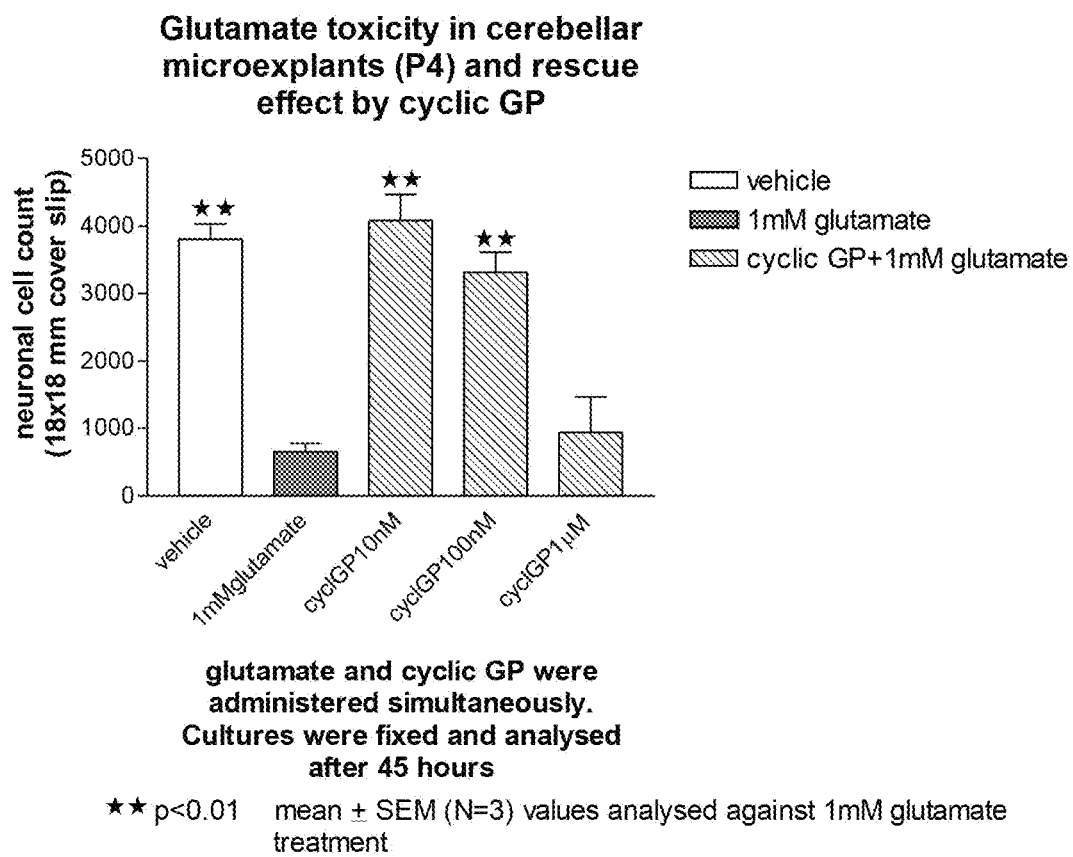
FIG. 3 illustrates in graphic form Glutamate toxicity in cerebellar microexplants (P4) and rescue effect by cyclic GP.

Cyclic PG Prevents Glutamate Induced Neuronal Death In Vitro in a Dose Related Manner Materials and Methods:
Cerebellar Cell Culture Preparing and Coating of Cover Slips Ten coverslips were placed into a large petri dish and washed in 70% alcohol for 5 minutes, then washed with Millipore $H_2O$. The coverslips were air dried, then coated with Poly-D-Lysine (1 mg/ml stock solution in PBS, 90-100 µl) and incubated for 2 hours at 34° C.
Extraction Postnatal day 4 Wistar rats were used for the study. Rats were placed in ice for 1 minute, the heads were decapitated and the cerebellum removed on ice. Cerebellum tissue was placed in 1 ml of 0.65% glucose supplemented PBS (10 µl 65% stock D (+)glucose/1 ml PBS) in a large petri dish, chopped up into smaller sections and triturate with a 1 ml insulin syringe via a 23 G (0.4 mm) needle, and then squirted back into the glucose solution on the large petri dish. The tissue was sieved through (125 µm pore size gaze) and centrifuged (2 minutes at 60 g) two times for a medium exchange into serum-free BSA-supplemented START V medium (Biochrom). The second centrifugation step was done with 1 ml of START V medium. The microexplants were reconstituted into 500 µl of START V medium and put on ice.
Cultivation and Fixation of Cerebellar Cells Two hours after PDL-coating, the slides were washed with Millipore $H_2O$ and air dried. Each slide was placed into a small 35 mm petri dish and 40 µl of START V/cell suspension added. The tissue was incubated for 2 hours at 34° C. (settlement period). START V-medium (1 ml) was then added to the petri dish and cultivated at 34° C./5% $CO_2$/100% humidity for 48 hours. Cells were rinsed in PBS and then fixed for 2-3 minutes in increasing concentrations of paraformaldehyde (500 µl of 0.4% PFA was applied; then 1.2% PFA; then 3% PFA and finally 4% PFA—all fixation solutions contain 0.2% glutardialdehyde). Finally, the microexplants were rinsed in PBS.
Drug Application 10 µl of toxin (L-glutamate-100 mM in Millipore water) was applied simultaneously with cPG (from bachem, 10 mM stock prepared in PBS and diluted to final concentrations between 1-100 nM) for Study 1. A delay in administration of cPG at 6 hours after glutamate treatment was performed for Study 2.
Result:

Study 1: Glutamate treatment resulted in 85% loss of cerebellum neurons. Cyclic PG significantly reduced the glutamate induced neuronal death in a dose response manner when administered simultaneously with glutamate (FIG. 3). The treatments with lower doses of cPG (10-100 nM) showed significant recovery from glutamate-induced neurotoxicity.

Figure 4:
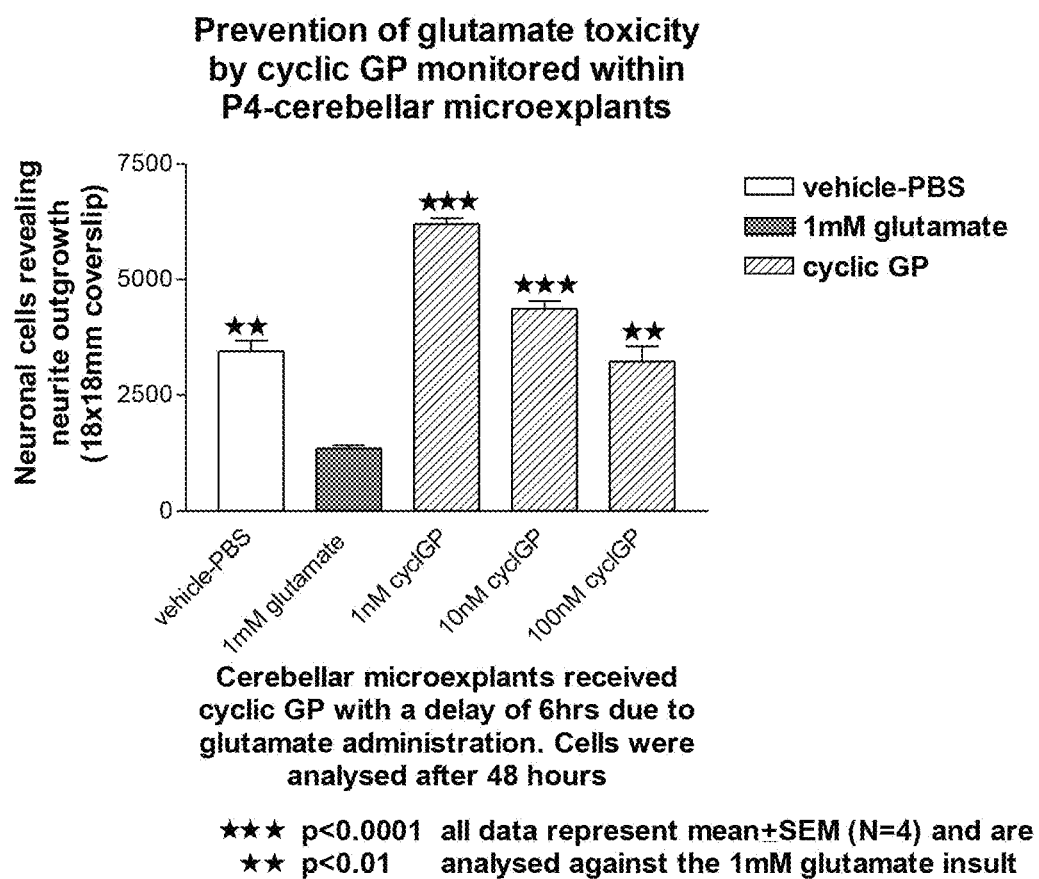
FIG. 4 illustrates in graphic form prevention of glutamate toxicity by cyclic GP monitored within P4-cerebellar microexplants.

Study 2: Cyclic PG showed a significantly recovery from glutamate induced neurotoxicity in a dose range of 1-100 nM when given 6 hours after the glutamate treatment compared to the vehicle treated group (FIG. 4).

A further lower dose of cPG also showed a significant increase in neuron number compared to the normal control group, suggest a role for cPG in neuronal proliferation and differentiation.
Conclusions Excessive glutamate can cause neuronal excitotoxicity by active NMDA receptors. cPG completely prevented the glutamate-induced neurotoxicity, when given either immediately or 6 hours after the glutamate treatment by acting as a direct or indirect NMDA agonist. Given that cPG can agonise mGlu2/3 receptor, which can inhibit NMDA activity. GPE, the pre-hormone for cPG has been shown to be partial NMDA receptor in promoting pCREB, probably due to its antic effect on mGlu2/3 receptors. cPG can be involved in preventing neurons undergoing apoptosis because cPG can be effective as a delayed treatment, and promoted the neuronal proliferation.

Experiment 2

Cyclic (tri(prolylglycyl)) or c(PG)3 Prevents Glutamate Induced Neuronal Death In Vitro in a Dose Related Manner Materials and Methods: (see above for Experiment 1, which is incorporated by reference herein.)
Drug Application 10 µl of toxin (L-glutamate-100 mM in Millipore water) was applied simultaneously with cyclic(tri(prolylglycyl)) (which was obtained from NeuroBiomed, San Jose, California), 10 mM stock prepared in PBS and diluted to final concentrations between 1-100 nM) for Study 1. A delay in administration of cyclic(tri(prolylglycyl)) at 6 hours after glutamate treatment was performed for Study 2.
Result:

Study 1: Glutamate treatment resulted in 85% loss of cerebellum neurons. cyclic(tri(prolylglycyl)) significantly reduced the glutamate induced neuronal death by 57% in a dose response manner when administered simultaneously with glutamate. The treatments with lower doses of cyclic (tri(prolylglycyl)) (10-100 nM) showed significant recovery from glutamate-induced neurotoxicity.

Study 2: cyclic(tri(prolylglycyl)) showed an improvement of approximately 43% significantly recovery from glutamate induced neurotoxicity in a dose range of 1-100 nM when given 6 hours after the glutamate treatment compared to the vehicle treated group.

A further lower dose of cyclic(tri(prolylglycyl)) also showed a significant increase in neuron number compared to the normal control group, suggest a role for cPG in neuronal proliferation and differentiation.

Experiment 3

Cyclic Glycyl-2-Methyl Proline Prevents Glutamate Induced Neuronal Death In Vitro in a Dose Related Manner Materials and Methods: (see above for Experiment 1 and Experiment 2, which is incorporated by reference herein)
Drug Application 10 µl of toxin (L-glutamate-100 mM in Millipore water) was applied simultaneously with cyclic Glycyl-2-Methyl Proline (obtained NeuroBiomed, San Jose California), 10 mM stock prepared in PBS and diluted to final concentrations between 1-100 nM) for Study 1. A delay in administration of cPG at 6 hours after glutamate treatment was performed for Study 2.
Result:

Study 1: Glutamate treatment resulted in 85% loss of cerebellum neurons. cyclic Glycyl-2-Methyl Proline significantly reduced the glutamate induced neuronal death by 63% in a dose response manner when administered simultaneously with glutamate. The treatments with lower doses of cyclic Glycyl-2-Methyl Proline (10-100 nM) showed significant recovery from glutamate-induced neurotoxicity.

Study 2: cyclic Glycyl-2-Methyl Proline showed an improvement of approximately 58% significantly recovery from glutamate induced neurotoxicity in a dose range of 1-100 nM when given 6 hours after the glutamate treatment compared to the vehicle treated group.

A further lower dose of cyclic Glycyl-2-Methyl Proline also showed a significant increase in neuron number compared to the normal control group, suggest a role for cPG in neuronal proliferation and differentiation.
Conclusions Excessive glutamate can cause neuronal excitotoxicity by active NMDA receptors. Cyclic PG analogues, cyclic(tri (prolylglycyl)) and cyclic Glycyl-2-Methyl Proline significantly prevented the glutamate-induced neurotoxicity, when given either immediately or 6 hours after the glutamate treatment by acting as a direct or indirect NMDA agonist.

Cyclic PG and its analogues, such as but not limited to cyclic(tri(prolylglycyl)) and cyclic Glycyl-2-Methyl Proline can be used in preventing neurons undergoing apoptosis because cPG compounds can be effective as a delayed treatment, and promoted the neuronal proliferation.

Experiment 4

Effects of cPG After 6-OHDA Induced Nigral-Striatal Lesion

Materials and Methods

Twenty male Wistar rats (280-310 g) were used. After exposing the skull, 6-OHDA (8 μg in a base of 2 μl 0.9% saline containing 1% ascorbic acid) was administered into the right medial forebrain bundle (MFB) using co-ordinates AP +4.7 mm, R 1.6 mmv −8 mm under 3% halothane anaesthesia. 6-OHDA was injected through a 25G needle connected via a polyethylene catheter to a 100 μl Hamilton syringe. The 6-OHDA was infused by a microdialysis infusion pump at a rate of 0.5 μl/min. The needle was left in the brain for a further 3 minutes before being slowly withdrawn. The skin was sutured with 2.0 silk and the rats were allowed to recover from anaesthesia. The rats were housed in a holding room with free access to food and water at all times except during behavioural testing.

Cyclic PG was dissolved in saline. Four different doses of cPG (0, 0.1, 0.5, 1 mg/kg, Bachem) were administered intraperitoneally 2 hours post lesion.

Figure 5:
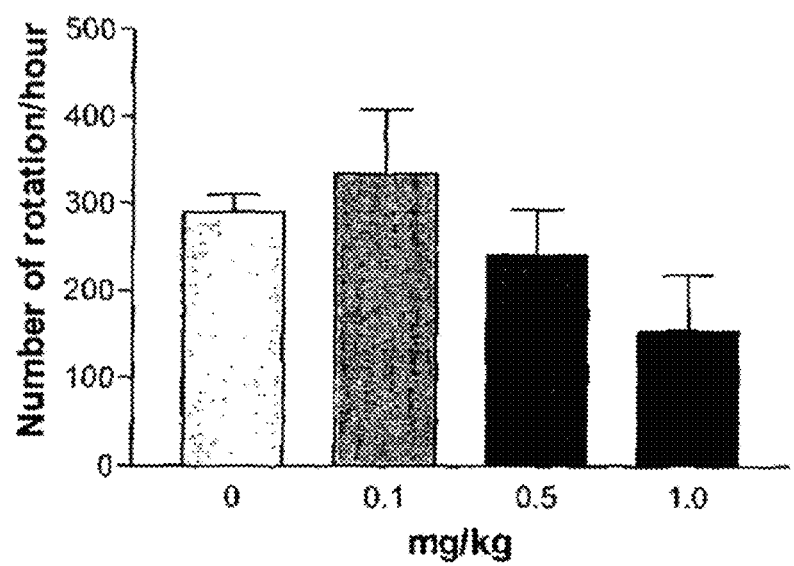
FIG. 5 illustrates in graphic form effects of cPG on functional recovery after 6-OHDA lesion.

At 7 days post-lesion, rats were injected with 0.1 mg/kg apomorphine and the number of contralateral rotations/hour was recorded and calculated using a computerised Rotameter (St Diego Instruments). Experimenter was blinded from the treatment groups.
Result:

The group treated with 1 mg cPG (n=5, 154±64) showed a trend toward a reduction in the number of rotations compared to the vehicle treated group (n=5, 290±18) indicating that cPG in improves functional recovery in 6-OHDA induced nigrostriatal injury. (FIG. 5).

Experiment 5

Effects of cyclic(tri(prolylglycyl)) After 6-OHDA Induced Nigral-Striatal Lesion Materials and Methods (see above for Experiment 1, Experiment 2, Experiment 3, and Experiment 4, which is incorporated by reference herein)

Cyclic(tri(prolylglycyl)) was dissolved in saline solution. Four different doses of Cyclic(tri(prolylglycyl)) (0, 0.1, 0.5, 1 mg/kg, NeuroBiomed) were administered intraperitoneally 2 hours post lesion.

The group treated with 1 mg cyclic(tri(prolylglycyl)) (n=5, 172±69) showed a trend toward a reduction in the number of rotations compared to the vehicle treated group (n=5, 290±18) indicating a role for cyclic(tri(prolylglycyl)) in improving functional recovery in 6-OHDA induced nigrostriatal injury.
Conclusions Cyclic(tri(prolylglycyl)) improved the functional recovery after 6-OHDA induced nigral-striatal lesions in a dose related manner.

This data indicates Cyclic(tri(prolylglycyl)) can be used as a treatment for Parkinson's disease and other neurological disorders.

Experiment 6

Effects of Cyclic Glycyl-2-Methyl Proline After 6-OHDA Induced Nigral-Striatal Lesion Materials and Methods (see above for Experiment 1 through Experiment 5, which are incorporated by reference herein).

Cyclic Glycyl-2-Methyl Proline (cGMeP) was dissolved in saline solution. Four different doses of cGMeP (0, 0.1, 0.5, 1 mg/kg, NeuroBiomed) were administered intraperitoneally 2 hours post lesion.

The group treated with 1 mg cGMeP (n=5, 134±69) showed a trend toward a significant reduction in the number of rotations compared to the vehicle treated group (n=5, 292±21) indicating a role for cGMeP in improving functional recovery in 6-OHDA induced nigrostriatal injury.
Conclusions Cyclic Glycyl-2-Methyl Proline improved the functional recovery after 6-OHDA induced nigral-striatal lesions in a dose related manner.

This data indicated that Cyclic Glycyl-2-Methyl Proline has efficacy as a treatment for Parkinson's disease.

Experiment 7

Morris Water Maze (MWM) Model of Learning and Memory Used to Assess Effects of Cyclic Prolyl Glycine on Cognitive Function cPG administered to animals treated with scopolamine-induced cognitive dysfunction produces clinical improvement in those animals, similar to the therapeutic improvement observed in people suffering from cholinergic hypofunction. Scopolamine is commonly used in animal models of cholinergic hypofunction associated with Alzheimer's disease. The functional deficits observed after scopolamine treatment include those found in human patients with Alzheimer's disease. Thus, scopolamine treatment is reasonably predictive of cognitive impairment found in human diseases. Additionally, scopolamine treatment mimics cognitive disfunctions in humans who do not have neurodegenerative disorders.

The purpose of the study was to investigate cyclic Prolyl Glycine to evaluate its impact cognitive deficit and affective state (anxiety).

Methods

The first part of the study involved acute testing of the cyclic Prolyl Glycine in the Morris Water Maze memory model. The MWM test is one of the most frequently used tests for assessing spatial memory in rats and is well recognized to accurately predict effects of disease and treatment on spatial memory generally. Therefore, the MWM test reflects effects of disease and treatment in human subjects.

The standard procedure for MWM was followed. We used a circular swimming pool (80 cm depth×150 cm diameter) filled with opaque water, with the temperature maintained at 20° C. A platform was hidden 1 cm below the water surface, with a white flag (10 cm×10 cm) located either 20 cm above the platform for the visual cue and at 3 o'clock position in relation to the starting location for a spatial cue. On days 1-4 of the experiment rats underwent memory acquisition trials with 6 trials (60 seconds each) in each day of testing (habituation phase). Latency to reach the platform was recorded and the daily reduction of average latency was used to measure the capability to learn where the hidden platform was.

On day 5 of the experiment normal, non-aged Wistar rats were split into groups to receive either saline (N=12) or scopolamine (0.5 mg/kg, i.p., N=12) to induce memory deficit. Scopolamine was administered half an hour before the probe test commenced.

10 min following the scopolamine treatment, the cyclic Prolyl Glycine was administered orally at 10 mg/kg (N=16) with vehicle-treated animals administered the diluent by oral gavage using an identical treatment protocol (n=15).

TABLE 1

Animals Used to Test Effects of cPG on Memory

|  | Scopolamine | Vehicle |
| --- | --- | --- |
| Vehicle | N = 12 | N = 12 |
| cPG | N = 16 | N = 15 |

Acute effects of cPG were then tested in animals with scopolamine-induced memory impairment and in age-matched control animals with no memory impairment to determine any direct pharmacological effect on memory processing. Experimental groups are detailed in the Table 1 below.

On day 5, the probe MWM test was performed with the platform removed. There were 6 trials, each of maximum duration of 60 s, at least 5 min rest between trials). The amount of time the rats spend swimming near the platform provided a measure of how much they relied on visual and spatial cue to locate the platform, as opposed to using a non-spatial strategy. Data was collected and analyzed using Any-maze (v4.2) software.

The data generated from behavioral tests was analyzed using one-way ANOVA for determining the difference between the aged-groups. Two-way ANOVA was used for examining the progress of behavioral results with the time points treated as dependent factors. GraphPad Prism version 3.02 was used for data analysis.

Results

Figure 6:
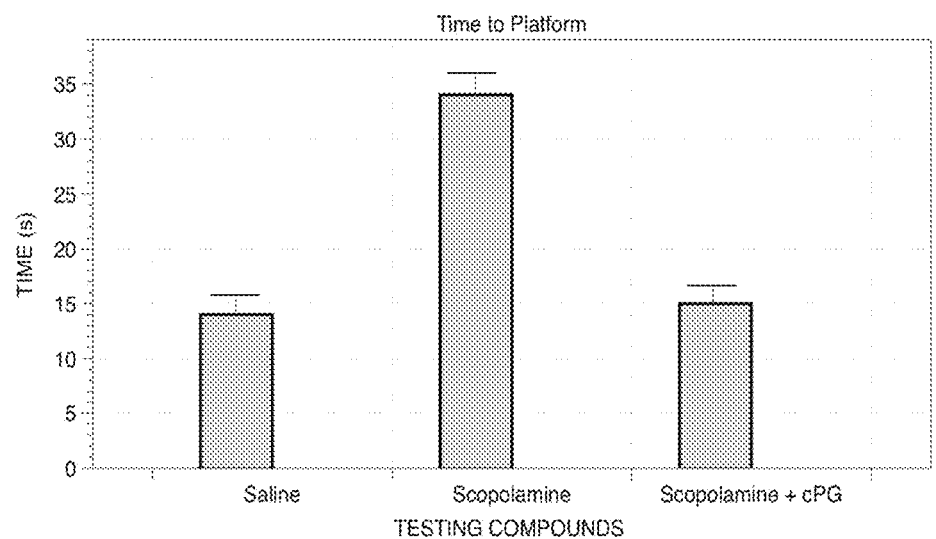
FIG. 6 illustrates the time to reach platform. Morris Water Maze (MWM) Model of Learning and Memory Used to Assess Effects of cyclic Prolyl Glycine on Cognitive Function.

Treatment with scopolamine significantly impaired acquisition of spatial memory in treated animals (time to platform approximately 208% of control on day 4). Cyclic Prolyl Glycine (20 mg/kg; daily) significantly reversed the cognitive impairment induced by scopolamine. (FIG. 6).

These results confirmed the presence of choline-positive effect in NA-831 on retrieval of learned skill of finding a submerged platform (spatial memory) and that this drug can be effective in patients with mild cognitive impairment.

Experiment 8

Determination of Neurogenesis by Testing cPG and its Analogues c(PG)3 and eGMeP with Bromodeoxyuridine Objective The objective of this experiment is to study the impact of intra-peritoneal infusion of cPG and its analogues c(PG)3 and cGMeP in rats, co-administered with BrdU in highly neurogenic regions including the sub ventricular zone and the dentate gyrus in the hippocampus.

Experimental Method:

Male Wistar rats weighing about 250-270 g (not newborn) were used. All animal experiments were conducted in agreement with national and international guidelines. Care was taken to minimize suffering for the animals. Animals were allowed to acclimatize for 1 week before start of the studies. Animals were housed under standardized conditions with normal tight-dark periods and in groups of five animals per cage. Animals had access to food and water ad libitum during the studies.

Three neurogenesis modulating agents, cPG, c(PG)3 and cGMeP were separately administered intraperitoneally to Male Wistar rats (N=10) at 10 mg/kg in Rat Serum Albumin (RSA). The negative control (n=12), the vehicle group was injected with saline (in 0.1% RSA). Bromodeoxyuridine (Brd1J; 50 mg/kg) was co-administered together with the compounds. The intraperitoneally injections were given with a 12 hour interval for 7 days. Animals were perfused on day 8. The rats were kept at 12 hours light/dark regime. In perfusion, animals were perfused transcranially with 50 ml of ice cold phosphate buffered saline (PBS) and then 100 ml of 4% paraformaldehyde in PBS. Brains were fixed after removal in 4% paraformaldehyde in PBS for 24 hours at 4° C. at least 3 days before sectioning. The procedures of transcranial infusion consist the following steps:

The animals were weighed to the nearest 0.1 grams and were administered with sodium pentobarbital and ketamine/xylazine. The animals were placed in a heated cage for 10-15 minutes. The rats were secured in the supine position (lying on the back with face upward) with its forepaws and hind paws pinned to a Styrofoam work surface inside a chemical fume hood. An incision was made through the skin with surgical scissors along the thoracic midline from just beneath the xiphoid process to the clavicle. Two additional skin incisions were made from the xiphoid process along the base of the ventral rib cage laterally. Gently reflect the two flaps of skin rostrally and laterally making sure to expose the thoracic field completely. The cartilage of the xiphoid process was grasped with blunt forceps and it was raised slightly to insert pointed scissors. The thoracic musculature and ribcage were cut through between the breastbone and medial rib insertion points and the incision was extended rostrally to the level of the clavicles. The diaphragm from the chest wall on both sides was separated with scissor cuts. The reflected ribcage was taped or pinned with 18G needles laterally to expose the heart and other thoracic organs. The pericardial sac was gently grasped with blunt forceps and was torn open fully. The beating heart was secured with blunt forceps and a 1-2 mm incision was made in the left ventricle. A 24G×25.4 mm animal feeding needle with a bulnous tip (Harvard apparatus Cat. #52-4009) was inserted. The feeding needle was thread into the base of the aortic arch using a dissecting microscope. The needle base was clamped to the left ventricle above the incision site using a hemostat. The right atrium was cut immediately with scissors and at the first sign of blood flow, the infusion of heparinized saline was started (stage 1 perfusate) and continued until the fluid exiting the right atrium is entirely clear. The saline perfusate was changed to aldehyde-based fixative (stage 2 perfusate) to a total of 20-30 ml of fixative as infused to an animal. The animal was decapitated with large surgical scissors. The brains were removed and embedded in paraffin, Sections were prepared using a freezing microtome and stored in cryoprotectant at −20° C. before immunostaining for BrdU. Sections were immunostained for BrdU with mouse anti-BrdU paired with a biotinylated goat anti mouse IgG and visualized using ABC Elite kit (Vectorlabs. using manufactures directions).

Standard light microscope techniques were used to count the total number of BrdU positive cells in each section and in relevant region of the brain. Analysis and quantification were performed for proliferative brain regions, subventricular zone, and the dentate gyros in hippocampus. Other experimental details not listed here are known to one of skill in the ail and may be found for example in Pencea V et al, J, Neurosci Sep. 1 (2001). 21(17):6706-17.

Results

Notably, it was found that rats given intra-peritoneal infusion of cPG, c(PG)3 and cGMeP at 10 mg/kg in 0.1% RSA, co-administered with BrdU twice daily showed a significant increase (nonparametric One-way ANOVA) in the number of newborn cells (BrdU positive compared to sham injected) in highly neurogenic regions including the sub ventricular zone and the dentate gyms in the hippocampus (FIG. 7 and FIG. 8).

Conclusion

In summary, the experiments demonstrated that cPG, c(PG)3 and cGMeP exhibit neural stem cell proliferative effect pointing to neugenesis.

Experiment 9

Determination of the Regeneration of Damaged Nerve Tissue with cPG

Postnatal day 4 Wistar 10 rats were used for the study. The rats were divided in 2 groups: one group of 5 animals treated with drug solution, and the other group of animals treated with 0.9% sodium chloride (saline) solution. A drug solution containing cPG (from Bachem, 10 mM solution prepared in 0.9% sodium chloride (saline) solution) was administered four times a day in volumes of 0.75 ml to thoroughly flood the site of injury.

Two days after crushing the spinal cord, the dura of a rat was opened and a polyethylene tube was sutured to the vertebral spines and adjacent soft tissues so that the opening in one end lay directly over the injured part of the spinal cord. The tubing was brought through a subcutaneous tunnel so that its other end emerged at the base of the skull. A syringe adapter was attached to the external opening for injecting the drugs. All experiments were on a double-blind basis on 2 groups: one group of 5 animals treated with drug solution of 10 mM in saline solution, and the other group of 5 animals treated with 0.9% sodium chloride (saline) solution. Treatment of every animal was continued for 14 days, after which the animals were killed and histological sections prepared.

Results

The drug treated animals showed greater invasion of the lesion by nerve fibers than did the vehicle treated with saline solution. In the drug-treated animals, the nerve fibers grew into the lesion site in such profusion that they were no longer oriented longitudinally, but grew rather haphazardly in all directions. Fibers were frequently undulating and varicose and were often arranged in small bundles containing 3-6 axons. The axons were very fine in calibers, most of them being 3-7 microns in diameter. When the slides were coded and randomized, there was no difficulty in distinguishing between the specimens from the drug-treated and the saline treated animals. The most prolific nerve growth occurred in the animals treated with cPG.

Conclusion

This Example showed that nerve regeneration is promoted by thoroughly bathing or otherwise contacting the injury site with the foregoing composition. The foregoing composition promotes regeneration of damaged nerve tissue when administered directly to the site of the injury.

Experiment 10

Regeneration of Damaged Nerve Tissue of Cyclic (glycyl-L-prolylglycyl-L-prolylglycyl-L-prolyl)

Postnatal day 4 Wistar 10 rats were used for the study. The rats were divided in 2 groups: one group of 5 animals treated with drug solution, and the other group of 5 animals treated with 0.9% sodium chloride (saline) solution. A drug solution containing 10 mM of cyclic (glycyl-L-prolylglycyl-1, prolylglycyl-D-prolyl) or c(PG)3, obtained from NeuroBiomed, San Jose, California. 10 mM solution prepared in 0.9% sodium chloride (saline) solution was administered four times a day in volumes of 0.75 ml to thoroughly flood the site of injury.

Two days after crushing the spinal cord, the dura of a rat was opened and a polyethylene tube was sutured to the vertebral spines and adjacent soft tissues so that the opening in one end lay directly over the injured part of the spinal cord. The tubing was brought through a subcutaneous tunnel so that its other end emerged at the base of the skull. A syringe adapter was attached to the external opening for injecting the drugs. All experiments were on a double-blind basis on 2 groups: one group of 5 animals treated with drug solution of 10 mM c(PG)3 in saline solution, and the other group of 5 animals treated with 0.9% sodium chloride (saline) solution. Treatment of every animal was continued for 14 days, after which the animals were killed and histological sections prepared.

Results

The results are similar to the above experiment with cPG. In the c(PG) treated animals, the nerve fibers grew into the lesion site in such profusion that they were no longer oriented longitudinally, but grew rather haphazardly in all directions. Fibers were frequently undulating and varicose and were often arranged in small bundles containing 3-6 axons. The axons were very fine in caliber, most of them being 3-7 microns in diameter.

When the slides were coded and randomized, there was no difficulty in distinguishing between the specimens from the drug-treated and the saline treated animals. The most, prolific nerve growth occurred in the animals treated with c(PG)3.

Nerve regeneration is promoted by thoroughly bathing the injury site with the foregoing composition. The foregoing composition promotes regeneration of damaged nerve tissue when administered to the site of the injury, including direct administration to the site of injury.

Experiment 11

Regeneration of Damaged Nerve Tissue of Cyclic Glycyl-2-Methyl Proline

Postnatal day 4 Wistar 10 rats were used for the study. The rats were divided in 2 groups: one group of 5 animals treated with drug solution, and the other group of animals treated with 0.9% sodium chloride (saline) solution. A drug solution containing 10 mM of cyclic Glycyl-2-Methyl Proline, or cGMeP (from NeuroBiomed, 10 mM solution prepared in 0.9% sodium chloride (saline) solution) was administered four times a day in volumes of 0.75 ml to thoroughly flood the site of injury.

Two days after crushing the spinal cord, the dura of a rat was opened and a polyethylene tube was sutured to the vertebral spines and adjacent soft tissues so that the opening in one end lay directly over the injured part of the spinal cord. The tubing was brought through a subcutaneous tunnel so that its other end emerged at the base of the skull. A syringe adapter was attached to the external opening for injecting the drugs. All experiments were on a double-blind basis on 2 groups: one group of 5 animals treated with drug solution of 10 cGMeP in saline solution, and the other group of 5 animals treated with 0.9% sodium chloride (saline) solution. Treatment of every animal was continued for 14 days, after which the animals were killed and histological sections prepared.

Results

The results are similar to the above experiment with cPG. In the cGMeP treated animals, the nerve fibers grew into the lesion site in such profusion that they were no longer oriented longitudinally, but grew rather haphazardly in all directions. Fibers were frequently undulating and varicose and were often arranged in small bundles containing 3-6 axons. The axons were very fine in caliber, most of them being 3-7 microns in diameter.

When the slides were coded and randomized, there was no difficulty in distinguishing between the specimens from the drug-treated and the saline treated animals. The most prolific nerve growth occurred in the animals treated with cGMeP.

Nerve regeneration is promoted by contacting, such as but limited to bathing the injury site with the foregoing composition. The foregoing composition promotes regeneration of damaged nerve tissue when administered directly to the site of the injury.

Experiment 12

Clinical Trial on Alzheimer's Patients with Mild Cognitive Impairment

Mild cognitive impairment ("MCI") is a syndrome defined as cognitive decline greater than expected for an individual's age and education level. Mild cognitive impairments are those involving impairments of memory and other cognition functions, beyond the age norm but not leading to the characteristic of dementia.

Mild cognitive impairment in population-based studies ranges from 3% to 15% in adults older than 65 years. More than half progress of people with MCI progress to dementia within 5 years.

The detection of mild cognitive disorders is important, because treatment can have the greatest efficacy at this stage than after dementia has developed.

Materials and Methods

A randomized clinical trial of NA-831 (also known as cyclic Prolyl Glycine) was performed on Alzheimer patients with mild cognitive impairment of vascular origin. The drug NA-831 was administered orally with a one capsule of 10 mg once a day over a period of 12 weeks. There were 32 Alzheimer patients participated in the study.

Inclusion Criteria
- Is male or female, at 55-85 years of age (inclusive) at screening.
- Self-reported memory complaint, corroborated by spouse or companion as appropriate.
- Wechsler Memory Scale III (WMS-III) age-adjusted Logical Memory II score ≤5.
- Mini-Mental State Exam (MMSE)≥24.
- Center for Epidemiologic Studies-Depression (CES-D) score <27.
- Normal thyroid function, defined as TSH, T3 and T4 within normal limits.
- Agree not to consume alcoholic beverages within 8 hours of each study visit.
- Willing and able to sign informed consent and complete the CTB and all other tests and procedures as listed in the protocol.
- Female subjects must be surgically sterile or post-menopausal for at least 2 years. If <2 years post-menopausal, then a follicle stimulating hormone (FSH) ≥40 mIU/mL must be obtained.

Exclusion Criteria:
- Subjects who have any significant, untreated psychiatric illness or any CNS condition (such as schizophrenia, Parkinson's disease, stroke, etc.) that could interfere with the study evaluations or procedures or which poses an additional risk.
- Subjects with a history of uncomplicated depression may participate if in remission and on a stable dose of antidepressant medication for at least 2 months.
- History of significant head trauma followed by persistent neurologic defaults or known structural brain abnormalities.
- Have had a stroke or Transient Ischemic Attack (TIA) or unexplained loss of consciousness in the past 1 year
- History of unstable angina, myocardial infarction, chronic heart failure or clinically significant conduction abnormalities within 1 year prior to Screening Visit 1
- History of alcohol or substance abuse or dependence within the past year.
- Acute infective sinusitis.
- History or presence of an abnormality of the external or internal structures of the nose or nasopharynx, except for surgical correction of the nasal septum or a "broken nose" at least 2 years previously, or surgical repair of cleft palate when <30 years of age.
- Use of medications that are known to cause frank obtundation of cognition Use of any approved or investigational medication for Alzheimer's Disease within 3 months of screening History of or current significant systemic disease judged to interfere with the study evaluations or likely to be a safety concern.

Untreated sleep apnea or treatment for sleep apnea for <3 months.

Clinically significant systemic illness or serious infection within 30 days prior to or during the screening period Use of allowed medications for chronic conditions at doses that have not been stable for at least 4 weeks prior to Screening Visit 1, or use of AD medications at doses that have not been stable for at least 8 weeks prior to Screening Visit 1.

Abnormal clinical laboratory test results, specifically: Alanine transaminase (ALT) or aspartate transaminase (AST) >2 x the upper limit of normal (ULN), Hematology <80% the lower limit of normal, Creatinine ≤2 mg/dL and other clinical laboratory values or vital signs considered clinically significant in the opinion of the Investigator.

Treatment with any investigational drug, biologic, or device within the previous 30 days prior to screening.

Surgery involving general anaesthesia within the past 3 months or planned surgery requiring general anaesthesia during the study period.

Contraindications to study procedures

Use of any medications that, in the opinion of the Investigator, may contribute to cognitive impairment, put the participants at higher risk for adverse events (AEs), or impair the participant's ability to perform cognitive testing or complete study procedures.

Assessment

1) A scale assessing the severity of symptoms based on the Unified Assessment of Clinical-Pharmacological Actions of Psychotropic Agents in Patients with Organic Disorders, which provides objective quantitative data on the therapeutic dynamics of psychopathological symptomatology and the characteristics of the psychotropic actions of agents.

2) The Mini Mental State Examination (MMSE), which consists of a battery of neuropsychological tests evaluating cognitive functions in points: attention, memory, gnosis, speech, praxis, and counting.

3) The Brief Cognitive Rating Scale (BCRS), which provides assessment of the severities of the individual components of cognitive impairments.

4) The Cognitive Capacity Screening Examination (CCSE), which consists of a battery of tests assessing cognitive functions: orientation, memory, counting, and the abilities to infer and to group objects.

5) The Clinical Global Impression scale, which provides quantitative assessments of the therapeutic efficacies of agents, along with tolerance and safety, using investigations of measures of disease severity, the level of "overall improvement," the therapeutic effect, and the presence and severity of side effects during treatment.

6) Laboratory analyses consisting of general blood and urine tests, including biochemical investigations (AST, ALT).

7) ECG traces.

Results

The mental state of patients with mild cognitive impairment, such as but not limited to through vascular origin was defined by the assessment including the Mini Mental State Examination (MMSE), the Brief Cognitive Rating Scale (BCRS), the Cognitive Capacity Screening Examination (CCSE).

The therapeutic actions of NA-831 in the patients includes decreases in neurosis-like symptomatology and cognitive disorders.

The results are given in Table 2:

TABLE 2

Mild Cognitive Impairment Measurement Data
Mild Cornitive Impairment - Clinical Data

| Measure | Baseline day 7 W | Baseline day 7 p | Baseline day 14 W | Baseline day 14 p | Baseline day 21 W | Baseline day 21 p | Baseline day 28 W | Baseline day 28 p | Baseline day 42 W | Baseline day 42 p | Baseline day 56 W | Baseline day 56 p | Baseline day 70 W | Baseline day 70 p |
|---|---|---|---|---|---|---|---|---|---|---|---|---|---|---|
| Increased fatigue | 17 | >0.05 | 95 | 0.02 | 97 | 0.02 | 137 | 0.01 | 155 | 0 | 159 | 0 | 162 | 0.001 |
| Anxiety | 22 | >0.05 | 22 | >0.05 | 46 | 0.02 | 70 | 0.02 | 107 | 0 | 110 | 0 | 115 | 0.001 |
| Decreased mood | 3 | >0.05 | 12 | >0.05 | 22 | 0.03 | 23 | 0.03 | 23 | 0 | 23 | 0 | 24 | 0.03 |
| Apathy indifference | 19 | 0.05 | 41 | 0.02 | 57 | 0.02 | 59 | 0.02 | 61 | 0 | 65 | 0 | 67 | 0.02 |
| Increased irritability | 38 | 0.02 | 47 | 0.02 | 68 | 0.01 | 93 | 0 | 109 | 0 | 110 | 0 | 117 | 0.001 |
| Affective Lability | 23 | 0.03 | 58 | 0.02 | 69 | 0.01 | 118 | 0.01 | 139 | 0 | 140 | 0 | 142 | 0.001 |
| Sleeping Disturbance | 37 | 0.03 | 47 | 0.02 | 70 | 0.02 | 70 | 0.02 | 82 | 0 | 82 | 0 | 82 | 0.01 |
| Disturbance to waking | 21 | >0.05 | 29 | 0.02 | 41 | 0.02 | 47 | 0.02 | 69 | 0 | 92 | 0 | 95 | 0.001 |
| Daytime drowsiness | 19 | >0.05 | 45 | 0.02 | 52 | 0.02 | 67 | 0.01 | 76 | 0 | 109 | 0 | 117 | 0.001 |
| Headache | 28 | 0.02 | 49 | 0.02 | 98 | 0 | 101 | 0 | 120 | 0 | 121 | 0 | 129 | 0.001 |
| Orthostatic Impairment | 18 | >0.05 | 37 | 0.02 | 58 | 0.02 | 78 | 0.01 | 67 | 0 | 78 | 0 | 81 | 0.02 |
| Tachycardia | 29 | 0.02 | 28 | 32 | 35 | 0.02 | 45 | 0.02 | 53 | 0 | 67 | 0 | 69 | 0.01 |
| Hyperesthesia | 11 | >0.05 | 21 | 0.03 | 33 | 0.04 | 67 | 0.01 | 69 | 0 | 78 | 0 | 83 | 0.01 |
| Sweating | 12 | >0.05 | 23 | >0.05 | 37 | 0.02 | 66 | 0.01 | 67 | 0 | 67 | 0 | 69 | 0.01 |
| Impairments to the depth and duration of nocturnal sleep | 37 | 0.02 | 57 | 0.02 | 91 | 0 | 93 | 0 | 104 | 0 | 113 | 0 | 118 | 0.001 |

W is Wilcoxon signed-rank test, which is the nonparametric test equivalent to the dependent t-test. It is used to compare two sets of scores that come from the same participants. This can occur when we wish to investigate any change in scores from one time point to another, or when individuals are subjected to more than one condition.

Clinicians use used a Wilcoxon signed-rank test to understand whether there was a difference in the patient conditions in term of fatigue before and after a period the time with the drug treatment.

Note that NA-831 has been shown to significantly improve the following functions with the p<0.01:
Reduce fatigue
Reduce anxiety
Reduce irritability
Improve lability
Reduce disturbance from waking up at night
Reduce daytime drowsiness
Improve duration of nocturnal sleep Analysis of the therapeutic efficacies of NA-831 were performed in all patients in the trial using the assessment methods including: the Mini Mental State Examination (MMSE), the Brief Cognitive Rating Scale (BCRS), and the Cognitive Capacity Screening Examination (CCSE).

The clinical data on the efficacy of NA-831 in Alzheimer patents can be summarized and highlighted as follows:

NA-831 was found to improve the patient's ability to concentrate and count. In the graph, the Measurement of Brief Cognitive Rating Scale was plotted against time, the statistical data after day 42 to day 84, with p value of less than 0.01. This means that they have significantly positive impacts in improving patients' concentration and ability to count. See, FIG. 9.

It is a common symptom that Alzheimer patients'short-term memory becomes progressively worse. NA-831 not only improves the short-term memory, but also long-term memory. See, FIG. 10.

In addition, Alzheimer patients' long term memory becomes progressively worse. NA-831 not only improves the short-term memory, but also long-term memory. See, FIG. 11.

In the early stages of the disease, Alzheimer patients often become disoriented even in their own home. NA-831 improves the orientation and restore their sense of time and place. See, FIG. 12.

As the disease progresses, Alzheimer patients cannot take care of themselves. The drug improves patient's ability to take care of their daily activity and self-care. See, FIG. 13.

The Mini—Mental State Examination (MMSE) is a 30-point questionnaire that is used extensively in clinical and research settings to measure cognitive impairment. The impact of NA-831 on the emotion of the patients were shown with a significant improvement in the MMSE from an average of 23.5 (mild impairment) on day 1 to 29.75 (normal) on day 84. See, FIG. 14.

NA-831 was found to have high efficacy in the treatment of patients with mild cognitive impairment with marked improvement in 92.5% of all patient, and little improvement in 7.5% of patients. See, FIG. 15.

Conclusions

Cyclic Prolyl Glycine decreased or prevented glutamate-induced neurotoxicity, indicating that the drug is neuroprotective and can be used to inhibit neuronal degeneration or cell death.

Experiment 13

Assay to Study the Relationship of cPG and NR2B-Subtype Receptors in Animals After Intravenous Administration In this experiment, 8-10 weeks old male CD-1 mice (n=12) were administered intravenously in a vehicle consisting of 10% dimethylacetamide, 40% PEG-400, 30% hydroxypropyl betacyclodextrin, and 30% water with cyclic Prolyl Glycine (0.10 mg: rill, and the forebrains were harvested 15 minutes post-dosing by decapitation. The brain samples were immediately frozen and stored at −80' C.

On the following day, the dosed brain samples were thawed on ice for 20-30 minutes followed by homogenization using Polytron for 10 seconds in cold homogenization buffer composed of 50 mM $KH_2PO_4$ (pH adjusted to 7.4 with KOH), 1 mM EDTA, 0.005% Triton X 100 and protease inhibitor cocktail (Fischer Scientific). The crude homogenates were further homogenized using a Bounce homogenizer (Thomas Scientific) and the homogenized membrane aliquots from all animals were gash-frozen and stored at −80° C. until further use. The whole homogenization process was performed on ice.

For determining occupancy, the membrane homogenates were thawed on ice and then needle homogenized using a 25-gauge needle. The homogenized membrane (64 mg/MO was added to a 96-well plate followed by addition of $^3H$ Ro 25-6981 (6 nM), The reaction mixture was incubated for 5 minutes on a shaker at and then harvested onto GF/B alter plates (treated with 0.5% PEI for 1 hour at room temperature). The alter plates were dried at 50"C for 30 mins, incubated with microscintillation 20 for 15 minutes and read by a benchtop microplate scintillation and luminescence counter (TopCount Model NXT manufactured by Perkin Elmer). Each dose or compound group consisted of 4 animals. The control group of animals was dosed with vehicle alone. Membrane from each animal was added in triplicates to the assay plate. Non-specific binding was determined using 10 µM Ro 25-6981 added to the wells containing membrane homogenates from vehicle-dosed animals.

Specific counts/minute was converted to % occupancy at each dose of a compound for each animal using the following equation:

$$\% \text{ Occupancy (animal } A) = \frac{\text{specific CPM of animal } A}{\text{Specific CPM from control group}} 100 - (\times 100)$$

Using this procedure cPG compound showed 93% NR2B receptor occupancy after a 3 mg/Kg i.v. dose. Drug levels were determined by mass spectroscopy method, Drug levels in the blood plasma were 1074 nM in at this dose, and drug levels in the homogenized brain tissue were 1632 nM.

The results indicate that cPG occupies brain-resident NR2B-subtype receptors in animals after intravenous administration and that the compound and its analogues are pharmaceutically effective.

Experiment 14

Mouse Forced Swim Test (mFST)

Forced Swim Test (FST) is an animal model used to assess antidepressant compounds in preclinical studies. The FST was performed similar to the method of Porsolt et al. with modifications (Porsolt R D, Bertin A, Jalfre M. Behavioral despair in mice: a primary screening test for antidepressants. Arch Int Pharmacodyn Thér 1977; 229:327-36).

In this experiment, mice are forced to swim in an inescapable cylinder filled with water. Under these conditions, mice will initially try to escape and eventually develop immobility behavior; this behavior is interpreted as a passive stress-coping strategy or depression-like behavior. Swim tanks were positioned inside a box made of plastic. Each tank was separated from each other by opaque plastic sheets to the height of cylinders. Three mice were subjected to test at a time. Swim sessions were conducted for 6 min by placing mice in individual glass cylinders (46 cm height×20 cm diameter) containing water (20-cm deep, maintained at 24-25° C.). At this water level, the mouse tail does not touch the bottom of the container. The mouse was judged to be immobile whenever it remained floating passively without struggling in the water and only making those movements necessary to keep its nose/head above the water and to keep it afloat. The duration of immobility was evaluated during the total 6 min of the test and expressed as duration (sec) of immobility. Each mouse was tested only once. At the end of each session, mice were dried with a dry cloth and returned to their home cage placed on a thermal blanket to prevent hypothermia. Water was replaced after each trial.

The results obtained in the FST were shown as an arithmetic mean of immobility time of animals (given in seconds)±standard error of the mean (SEM) for each experimental group.

In order to avoid the risk of obtaining the false positive\negative effects in the FST caused by a possible influence of the tested drugs on the locomotor activity, spontaneous locomotor activity was measured using an animal activity meter Opto-Varimex-4 Auto-Track (Columbus Instruments, USA). The device consists of four transparent cages with a lid (43×43×32 cm), a set of four infrared emitters (each emitter has 16 laser beams), and four detectors monitoring animal movements. Each mouse was placed individually into the cage for 10 min. Spontaneous locomotor activity was evaluated between the $2^{nd}$ and the $6^{th}$ min, which corresponds with the time interval analysed in the FST.

In addition, all testing sessions were recorded with a video camera (Sony Handicam, Model: DCR-HC38E; PAL) and scoring was done using the Forced Swim Scan, Version 2.0 software (Clever Systems Inc., Reston, Va., USA; see Hayashi E, Shimamura M, Kuratani K, Kinoshita M, Hara H. Automated experimental system capturing three behavioral components during murine forced swim test. Life Sci. 2011 Feb. 28; 88(9-10):411-7 and Yuan P, Tragon T, Xia M, Leclair C A, Skoumbourdis A P, Zheng W, Thomas C J, Huang R, Austin C P, Chen G, Guitart X. Phosphodiesterase 4 inhibitors enhance sexual pleasure-seeking activity in rodents. Pharmacol Biochem Behav. 2011; 98(3):349-55).

Cyclic Prolyl Glycine (at concentration 0.10 mg/ml) was administered in 12 mice thirty minutes before swim session by i.v. route and immobility time was recorded for next 6 min. At the end of FST, the mouse was euthanized by rapid decapitation method and plasma and brain samples were collected and stored under −80° C. till further analysis. In the mouse forced swim assay, the cPG compound was dosed intravenously in a vehicle of saline solution (0.90% Sodium Chloride) at a 5 mL/Kg dosing volume. The compound demonstrated a statistically significant decrease in immobility time at 1 mg/Kg under these conditions. Drug levels were 237+/−128 nM in the plasma and 632+/−173 nM in the brain at this dose. The NR2B receptor occupancy was determined as reported above and was determined to be 73%. The cPG analog demonstrated a statistically significant decrease in immobility time at 1 mg/Kg under these same conditions. Drug levels were 215 nM in the plasma. The NR2B receptor occupancy was determined to be 68%.

The results indicate that cyclic Prolyl Glycine (NA-831) compounds exhibit antidepressant properties.

Experiment 15

Clinical Study: A Double-Blind, Randomized, Placebo-Controlled, Active Reference Study of Cyclic Prolyl Glycine (NA-831) in Patients with Major Depressive Disorder Introduction Cyclic Prolyl Glycine (NA-831) is a novel compound under development as an antidepressant. Based on preclinical data, these affinities are considered to be of clinical relevance and involved in the mechanism of action at therapeutic doses. In vivo, NA-831 increases the extracellular levels of serotonin (5-HT), noradrenaline, dopamine, acetylcholine and histamine in rat prefrontal cortex and hippocampus. The aim of this clinical study was to investigate the efficacy, safety, and tolerability of two fixed doses (2.0 and 40 mg/d) of NA-831 vs. that of placebo after 6 week treatment in adult patients with major depressive disorder (MDD). Venlafaxine XR was used as the active reference.

Method

This randomized, double-blind, fixed-dose, placebo-controlled, active reference study recruited 32 randomized patients in accordance with the principles of Good Clinical Practice [ICH (1996). Harmonized Tripartite Guideline E6: Guideline for Good Clinical Practice (http://www.fda.gov/downloads/drugs/guidancecomplianceregulatoryinformation/gui dances/ucm073122.pdf)] and the Declaration of Helsinki [WMA (1964). Ethical Principles for Medical Research Involving Human Subjects (http://www.wma.net/en/30publications/10policies/b3/). World Medical Association.] Local ethics committees approved the study design and eligible patients gave their written informed consent before participating.

Eligible patients were randomized equally (1:1:1:1) to one of the four treatment arms for a 6-week double-blind treatment period. Randomized patients were given 1-week wallet cards at each visit and were instructed to take two capsules per day, orally, at the same time every day (preferably in the morning). NA-831 was dosed at 20 mg/day or 40 mg/d for 6 week and venlafaxine at 75 mg/d over 6-week treatment period. Efficacy and tolerability were assessed at screening, baseline and after 1, 2, 3, 4, 5, and 6 week. Patients were contacted for a safety follow-up 4 week after the completion visit.

Main Entry Criteria

Patients with MDD presenting with a current major depressive episode according to DSM-IV-TR criteria were included in the study if they were an outpatient of either sex, aged from 20 yr to 65 yr, (mean=39.7±8.5) (with a Montgomery—Åsberg Depression Rating Scale (MADRS) (Montgomery & Åsberg, 1979) total score ≥30 at the baseline visit. [Montgomery S Åsberg M (1979). A new depression scale designed to be sensitive to change. British Journal of Psychiatry 134 382-389.https://doi.org/10.1192/bjp.134.4.382]

Patients were excluded if they had any current psychiatric disorder other than MDD as defined in Diagnostic and Statistical Manual of Mental Disorders, $4^{th}$ Edition (DSM- IV-TR), assessed using the Mini International Neuropsychiatric Interview [Sheehan D V Lecrubier Y Sheenan K H Amorim P et al. (1998). The Mini-International Neuropsychiatric Interview Journal of Clinical Psychiatry 59 (Suppl. 20), 22-33, quiz 34-57] or if they had a current or past history of manic or hypomanic episode, schizophrenia or any other psychotic disorder, including major depression with psychotic features, mental retardation, organic mental disorders, or mental disorders due to a general medical condition, any substance abuse disorder) within the previous 6 months, presence or history of a clinically significant neurological disorder (including epilepsy), any neurodegenerative disorder, or any Axis II disorder that might compromise the study.

Patients at serious risk of suicide, based on the investigator's clinical judgement, or who had a score of ≥5 on item 10 of the MADRS scale (suicidal thoughts) were also excluded, as were those receiving formal behaviour therapy or systematic psychotherapy, or were pregnant or breastfeeding, had a known hypersensitivity or were non-response to venlafaxine, or whose current depressive symptoms were considered by the investigator to have been resistant to two adequate antidepressant treatments of at least 6 week duration, or had previously been exposed to NA-831.

Patients were also excluded if they were taking the following psychotropic drugs within 2 week prior to baseline or during the study: Reversible or irreversible monoamine oxidase inhibitors, SSRIs (fluoxetine within 5 week), SNRIs, tricyclic antidepressants, psychoactive herbal remedies, any drug used for augmentation of antidepressant action or any other antidepressant drugs, oral antipsychotic and anti-manic drugs, or dopamine ants, any anxiolytics (including benzodiazepines); and any anticonvulsant drug, serotonergic s, narcotic analgesics or cough agents, antiarrhythmics, oral anticoagulants, proton pump inhibitors, steroids, cisapride, macrolide antibiotics, antifungal agents, antihypertensives, all anti-inflammatory agents, anti-migraine agents, pseudoephedrine, hypolipidaemics, and episodic use of insulin. Occasional use of zolpidem, zopiclone and zaleplon for insomnia was allowed.

Patients were withdrawn if they became pregnant during the study, if the investigator considered it to be in the best interest of the patient for safety/efficacy reasons, if laboratory values were outside normal ranges and clinically significant, if they were considered to be at significant risk of suicide, if they scored ≥5 points on item 10 (suicidal thoughts) of the MADRS, if the randomization code for a patient was broken, if consent to participate was withdrawn, if they did not take study medication for more than 6 consecutive days, or if the patient was lost to follow-up. The patient could be withdrawn from the study if a serious adverse event (SAE) occurred. If adverse events (AEs) were contributory to withdrawal, they were always regarded as the primary reason for withdrawal.

Efficacy Rating

Patients were evaluated using the MADRS from baseline to week 6. Rater training was undertaken to increase inter-rater reliability, and was supervised by an experienced investigator. Only those investigators who had actively participated in rater training sessions prior to inclusion of patients into the study were allowed to rate patients. Patient ratings were assessed by the same investigator at each visit, whenever possible.

Allocation to Treatment

The medication was given as capsules of identical appearance. Patients who met the selection criteria at the baseline visit were assigned to double-blind treatment according to a computer-generated randomization list. The details of the randomization series were unknown to any of the investigators and were contained in a set of sealed opaque envelopes. At each study site, sequentially enrolled patients were assigned the lowest randomization number available in blocks of four. All investigators, study personnel and participants were blinded to treatment assignment for the duration of the entire study.

Analysis Sets

All safety analyses were based on the all-patients-treated set (APT), comprising all randomized patients who took at least one dose of study medication. All efficacy analyses were based on a modified intent-to-treat set (ITT)—the full-analysis set (FAS), comprising all patients in the APIS who had at least one valid post-baseline MADRS total score assessment.

Primary Efficacy Analysis

Four hypotheses were part of the primary efficacy analysis, which was fully adjusted for multiplicity using a hierarchical testing procedure at the 5% level of significance as long as the previous hypothesis was rejected. The order of testing was: no difference between the 20 mg dose vs. placebo at week 6, no difference between mg vs. placebo at week 6, no difference between 20 mg dose vs. placebo at week 1, and finally no difference between 40 mg dose vs. placebo at week 1. The statistical model was an analysis of covariance (ANCOVA) of the change from baseline in MADRS total score (FAS, LOCF) with treatment and site as fixed factors and the baseline MADRS score as a covariate. The primary efficacy analysis was repeated on observed cases (OC) data, using both an ANCOVA and a mixed model for repeated measurements (MMRM).

Tolerability Assessments

All adverse effects (AEs) (including any change in concurrent illnesses or new illnesses) either observed by the investigator or reported spontaneously by the patient were recorded. AEs were coded using the lowest level term according to the Medical Dictionary for Regulatory Activities, version 10.0. As a post-hoc analysis, the safety database was searched at preferred-term and verbatim-term level for possible suicide-related AEs, as described by the FDA [Laughren (2006). Memorandum on Suicidality. (http://www.fda.gov/ohrms/dockets/ac/06/briefing/2006-4272b1-01-fda.pdf)].

Results

Patient Baseline Characteristics

The APTS comprised 32 patients (placebo, 8; venlafaxine, 8; 20 mg NA-831, 8; 40 mg NA-831,8). There were no clinically relevant or statistically significant differences between the treatment groups in patient demographics or clinical characteristics at baseline (Table 3) Patients had a mean age (±S.D.) of 39.7±8.5 yr, 59.4% were women. The mean baseline MADRS total score was 34.0, indicating a severely depressed patient population, consistent with the mean CGI-S score of 5.1. Patients were diagnosed with their first MDE ~10 yr prior to enrolment. Between 74% and 80% of the patients in each treatment group had had a previous MDE and their current episode had started about 5 months prior to enrolment.

TABLE 3

Baseline patient characteristics

|  | Placebo (n = 8) | NA-831 20 mg (n = 8) | NA-831 40 mg (n = 8) | Venlafaxine 225 mg (n = 8) |
|---|---|---|---|---|
| Women | 5 (62.5% | 5 (62.5%) | 5 (50.0%) | 5 (62.5%) |
| Age (yr) | | | | |
| Mean ± SD | 40.0 ± 10.7 | 41.3 ± 8.9 | 39.6 ± 10.4 | 38.0 ± 10.3 |
| Range | 21-61 | 21-62 | 19-60 | 20-63 |
| Patients with first MDE | 21.50% | 22.50% | 23.00% | 22.50% |
| Years since first MDE ± SD. | 10 ± 4 | 10 ± 3 | 9 ± 3 | 11 ± 9 |
| Days since start of current MDE ± SD | 165 ± 34 | 161 ± 39 | 163 ± 35 | 160 ± 47 |
| Efficacy scores | (n = 105) | (n = 108) | (n = 100) | (n = 112) |
| MADRS total score ± SD | 33..4 ± 2.7 | 34.1 ± 2.6 | 34.0 ± 2.8 | 33.2 ± 3.1 |

Based on the full-analysis set: CGI-S, Clinical Global Impression - Severity; MADRS: Montgomery-Åsberg Depression Rating Scale;
MDE: major depressive episode;
S.D.: standard deviation.

Withdrawals from the Study

Only 4 subjects withdrew because of various reason: one from the placebo group, one from the 40 mg NA-831 group and 2 from the Venlafaxine group. More than 87% of the patients completed the study.

Efficacy

On the pre-defined primary efficacy endpoint, both doses of NA-831 were statistically significantly ($p<0.0001$) superior to placebo in mean change from baseline in MADRS total score at week 6 (FAS, LOCF), with mean treatment differences to placebo of 7.7 (20 mg) and 8.5 (40 mg) points (Table 4) in a multiplicity-controlled analysis. Venlafaxine was also statistically significantly ($p<0.0001$) superior to placebo at week 6, with a mean treatment difference to placebo of 7.2 points (LOCF). The estimated treatment differences and nominal p values at week 6 obtained from an analysis using MMRM were similar to those obtained in the ANCOVA analyses 5.7±1.3 (20 mg NA-831), 7.8±1.3 (40 mg NA-831), 5.6±1.3 (venlafaxine), all $p<0.0001$] (Table 2).

TABLE 4

Summary of Efficacy Analysis

| Analysis | Treatment Group | Mean ± SD | Difference to Placebo | p value |
|---|---|---|---|---|
| LOCF, ANCOVA | Placebo (n = 7) | -14.7 ± 1.0 | — | — |
|  | NA-831 20 mg (n = 8) | -22.4 ± 1.0 | -7.7 ± 1.4 | <0.0001 |
|  | NA-831 40 mg (n = 7) | -23.2 ± 1.0 | -8.5 ± 1.4 | <0.0001 |
|  | Venlafaxine (n = 6) | -21.9 ± 1.0 | -7.2 ± 1.4 | <0.0001 |
| OC, ANCOVA | Placebo (n = 7) | -16.6 ± 1.0 | — | — |
|  | NA-831 20 mg (n = 8) | -22.3 ± 0.9 | -5.7 ± 1.3 | <0.0001 |
|  | NA-831 40 mg (n = 7) | -24.4 ± 1.0 | -7.8 ± 1.3 | <0.0001 |
|  | Venlafaxine (n = 6) | -22.2 ± 0.9 | -5.6 ± 1.3 | <0.0001 |
| MMRM | Placebo (n = 7) | -15.4 ± 1.0 | — | — |
|  | NA-831 20 mg (n = 8) | -22.3 ± 0.9 | -6.9 ± 1.3 | <0.0001 |
|  | NA-831 40 mg (n = 7) | -24.9 ± 1.1 | -9.5 ± 1.4 | <0.0001 |
|  | Venlafaxine (n = 6) | -23.5 ± 0.9 | -8.1 ± 1.3 | <0.0001 |

FAS: Full-analysis set
LOCF: last observation carried forward
MADRS: Montgomery-Åsberg Depression Rating Scale;
MMRM: mixed model repeated measures;
OC: observed cases;
S.E., standard error of the mean.

Tolerability and Safety

During the 6-week treatment period, approximately 60% of patients in the placebo group and 75% of the venlafaxine groups had one or more AN. Only 12.5% of 20 mg NA-831 groups and 12.5% of the patients in the 40 mg NA-83 had AEs.

A total of 10 (33.3%) patients withdrew due to AEs: 1 (10%) in the placebo group, no withdrawal from the 20 mg NA-831 group, 1 (12.5%) in the 20 mg NA-831 group, and 2 (25%) in the venlafaxine group.

The most common AEs reported in the active NA-831 treatment groups were mild headache and dry mouth. A majority of patients in the venlafaxine group reported nausea, severe headache loss of strength, blurred vision, chest pain, fast or irregular heartbeat and suicidal thoughts.

Conclusion

The aim of the double-blind, randomized, placebo-controlled study was to evaluate the efficacy, safety and tolerability of NA-831 in patients with MDD. The active reference, venlafaxine XR was included with the purpose of validating the study methodology and patient population, and was effective on the primary efficacy analysis. Both doses of NA-831 resulted in a significant improvement compared to placebo on the primary efficacy analysis.

The difference between active treatment and placebo of ~7 points on the MADRS translates into a clinically relevant difference in response rates of 32.5 units, compared to an average of 16% units for antidepressants approved by the European authorities [ Melander H Salmonson T Abadie E van Zwieten-Boot B (2008). A regulatory apologia—A review of placebo-controlled studies in regulatory submissions of new-generation antidepressants. European Neuropsychopharmacology 18, 623-627.https://doi.org/10.1016/j.euroneuro.2008.06.003]

In conclusion, treatment with NA-831 for 6 week in this study was well tolerated and efficacious in reducing depressive and anxious symptoms in patients with MDD.

The present invention is described with reference to specific embodiments thereof. Other features and embodiments of this invention can be produced by those of skill in the art without undue experimentation and a reasonably likelihood of success. All of those and other embodiments are considered to be part of this invention.

Advantages of the Present Invention

Some advantages offered by the present invention with the cyclic peptides, especially over IGF-I include:

The active ingredients are easy to synthesize either in vitro or by other means such as recombinant techniques.

The peptide as a small molecule can diffuse readily through the body and between compartments (e.g. the blood-brain barrier, and mucous membranes), aiding in the choice of methods for its administration and its ability to reach sites where injury has occurred.

cPG, c(PG)3 and cGMeP are very stable molecule and is unlikely to present a challenge to the immune system, so it may be administered over extended periods and it may be administered prophylactically.

The present invention provides a novel therapeutic method for preventing brain injury and degenerative diseases by regulating mGluRs particularly 2/3 leading to long-term benefits of brain recovery.

With a role in regulating IGF-1 induction, cPG will provide further neuroprotection with less potential for growth side-effects.

Conclusions

Cyclic Prolyl Glycine decreased or prevented glutamate-induced neurotoxicity, indicating that the drug is neuroprotective and can be used to inhibit neuronal degeneration or cell death.

The present invention is described with reference to specific embodiments thereof. Other features and embodiments of this invention can be produced by those of skill in the art without undue experimentation and a reasonably likelihood of success. All of those and other embodiments are considered to be part of this invention.

While various embodiments of the present invention have been described above, it should be understood that they have been presented by way of examples only, and not limitation. It will be understood by those skilled in the art that various changes in form and detail may be made therein without departing from the spirit and scope of the present invention as defined in the appended claims. Thus, the breadth and scope of the present invention should not be limited by any of the above-described exemplary embodiments, but should be defined in accordance with the following claims and their equivalents.

All publication, including patent documents and scientific articles, referred to in this application, including any bibliography, are incorporated by reference in their entirety for all purposes to the same extent as if each individual publication were individually incorporated by reference. All headings are for the convenience of the reader and should not be used to limit the meaning of the text that follows the heading, unless so specified.

What is claimed is:

1. A method of treating, relieving, or alleviating major depressive disorder in a mammal, comprising:
   a) providing a mammal in need of treating, relieving, or alleviating major depressive disorder;
   b) administering a pharmaceutically effective amount of cyclic Prolyl Glycine (cPG) or its analogues (cyclic(tri (Prolyl Glycine) or cyclic Glycyl-2-Allyl Proline, or cyclic Glycyl-Alkyl Proline or cyclic Glycyl-2-Methyl-Proline (cPMeG), or a combination thereof, collectively called a cPG compound, to said mammal;
   wherein said mammal is treated, relieved, or alleviated of major depressive disorder.
2. The method of claim 1, wherein said pharmaceutically effective amount of said cPG compound is from about 1 μg to about 100 mg per kg of body weight.
3. The method of claim 1, wherein said pharmaceutically effective amount of said cPG compound is administered at an amount from about 0.1 mg to about 10 mg/kg per day, from about 0.5 mg to about 20 mg/kg per day, from about 0.2 mg to about 40 mg/kg per day, from about 5 mg to about 50 mg/kg per day, or from about 10 micrograms to about 100 mg/kg per day.
4. The method of claim 1, wherein said pharmaceutically effective amount or said cPG compound has a lower limit of about 0.1 milligrams per kilogram mass (mg/kg) of said mammal and an upper limit of about 10 mg/kg of said mammal.
5. The method of claim 1, wherein said pharmaceutically effective amount of said cPG compound is between about 20 mg and about 80 mg per day, or between about 20 mg and about 100 per day.
6. The method of claim 1, wherein said administering is in the form of a pharmaceutical composition including a pharmaceutically acceptable carrier.
7. The method of claim 1, wherein said administering is in combination with artificial cerebrospinal fluid.
8. The method of claim 1, wherein said administering is intravenous.
9. The method of claim 1, wherein said administering is combined with the administration of a neuroprotective agent, insulin-like growth factor-I (IGF-I) insulin growth-like factor-II (IGF-II), or a combination thereof.
10. The method of claim 1, wherein said administering is combined with the administration of an anti-inflammatory agent, an anti-integrin alpha 4 subunit agent, or a combination thereof.
11. The method of claim 1, wherein said administering is combined with administration of an anti-inflammatory agent.
12. The method of claim 1, wherein said cPG compound is provided in aqueous solution and one or more pharmaceutically acceptable excipients, additives, carriers, adjuvants, or a combination thereof.
13. The method of claim 1, wherein said cPG compound comprises one or more pharmaceutically acceptable excipients, carriers, additives, adjuvants, binders, or a combination thereof.
14. The method of claim 1, wherein said pharmaceutically effective amount of said cPG compound is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, vaginal, or a combination thereof.
15. The method of claim 1, wherein said mammal is human.
16. The method of claim 1, wherein said cPG compound is in the form of a table, capsule, or a combination thereof.
17. The method of claim 1, wherein said treating, relieving, or alleviating is treating.
18. The method of claim 1, wherein said treating, relieving, or alleviating is relieving.
19. The method of claim 1, wherein said treating, relieving, or alleviating is alleviating.

* * * * *

UNITED STATES PATENT AND TRADEMARK OFFICE
CERTIFICATE OF CORRECTION

| | | |
|---|---|---|
| PATENT NO. | : 12,070,458 B2 | |
| APPLICATION NO. | : 18/315910 | |
| DATED | : August 27, 2024 | |
| INVENTOR(S) | : Lloyd Hung Loi Tran | |

It is certified that error appears in the above-identified patent and that said Letters Patent is hereby corrected as shown below:

On the Title Page

Item (54) and in the Specification, Column 1, Lines 1-5, In the title, "CONGNITIVE" should be removed and --COGNITIVE-- should be added.

Signed and Sealed this
Fifteenth Day of October, 2024

Katherine Kelly Vidal
*Director of the United States Patent and Trademark Office*